United States Patent [19]
Schwarz et al.

[11] Patent Number: 5,629,468
[45] Date of Patent: May 13, 1997

[54] ROOT STIMULATING BACTERIA

[75] Inventors: Otto J. Schwarz, Knoxville, Tenn.; John A. Burns, Stillwater, Okla.; Beth C. Mullin, Knoxville, Tenn.

[73] Assignee: Universtiy of Tennessee Research Corporation, Knoxville, Tenn.

[21] Appl. No.: 354,656

[22] Filed: Dec. 13, 1994

Related U.S. Application Data

[63] Continuation-in-part of Ser. No. 249,901, May 26, 1994.

[51] Int. Cl.$^6$ .................... A01H 5/00; A01N 63/00; C12N 1/00
[52] U.S. Cl. .................... 800/200; 800/DIG. 47; 800/DIG. 49; 800/DIG. 51; 435/243; 435/252.1; 424/93.4
[58] Field of Search .................... 800/200, DIG. 47, 800/DIG. 49, DIG. 51; 435/243, 252.1; 424/93.4

[56] References Cited

U.S. PATENT DOCUMENTS

| | | | |
|---|---|---|---|
| 4,297,125 | 10/1981 | Haissig et al. | 71/77 |
| 4,353,184 | 10/1982 | El-Nil | 47/58 |
| 4,863,506 | 9/1989 | Young | 71/113 |
| 5,059,241 | 10/1991 | Young | 71/106 |
| 5,168,059 | 12/1992 | Roberts | 435/240.45 |
| 5,229,114 | 7/1993 | Cregan et al. | 424/93 |
| 5,236,841 | 8/1993 | Gupta et al. | 435/240.45 |
| 5,240,839 | 8/1993 | Serres et al. | 435/172.3 |
| 5,276,005 | 1/1994 | Lorina et al. | 424/195.1 |

FOREIGN PATENT DOCUMENTS

WO9013219  11/1990  WIPO.

OTHER PUBLICATIONS

Magnussen, D. et al., "Induction of Hairy and Normal Roots on *Picea abies*, *Pinus sylvestris* and *Pinus contorta* by *Agrobacterium rhizogenes*", Biological Abstracts, vol. 97, Abstract No. 171942 (1994).

Rinallo, C. et al., "Rooting of *Castanea sativa* Mill. shoots: Effect of *Agrobacterium rhizogenes* T–DNA genes", Journal of Horticultural Science, 68:(3)399–407 (1993).

Rodriguez–Barrueco, C. et al., "Growth Promoting Effect of *Azospirillum brasilense* on *Casuarina cunninghamiana* Mig. seedlings", Plant and Soil, 135:121–124 (1991).

Fernanadez, C. et al., "IAA Production by Microorganisms from the Sugarcane Rhizoplane", Biological Abstracts, vol. 91, Abstract No. 134453.

Koga, J. et al., "Molecular Cloning of the Gene for Indolepyruvate Decarboxylase from *Enterobacter Cloacae*", Mol Gen Genet., 226:10–16 (1991).

Brown, M. E., "Plant Growth Substances Produced by Micro–organisms of Soil and Rhizosphere", J. Appl. Bact., 35:443–451 (1972).

Blakesley, D., "Auxin Metabolism and Adventitious Root Initiation," Biology of Adventitious Root Formation, Basic Life Sciences, vol. 62, Plenum Press, 1994.

Burns, J. A., O. J. Schwarz, and S. E. Schlarbaum. 1991. Multiple shoot production from seedling explants of slash pine (*Pinus elliottii*, Englem.). Plant Cell Reports. 10: 439–443.

(List continued on next page.)

Primary Examiner—Douglas W. Robinson
Assistant Examiner—Elizabeth F. McElwain
Attorney, Agent, or Firm—Weiser & Associates, P.C.

[57] ABSTRACT

A bacteria which stimulates root production, or an extract in which the bacteria had been growing, is contacted to a portion of a plant other than a root. The root stimulating bacteria (RSB) or the extract induces the formation of roots in the plant. The RSB is well suited for inducing rooting in difficult to root species such as conifers of the Pinus genus. The RSB, the extract, the medium in which the RSB grows, the method for use of the RSB or the extract to induce rooting, and the plants treated with the RSB or the extract comprise the current invention.

34 Claims, 15 Drawing Sheets

OTHER PUBLICATIONS

Gay, G., "Effect on the ectomycorrhizal fungus *Hebeloma hiemale* on adventitious root formation in derooted *Pinus halepensis* shoot hypocotyls", Canadian Journal of Botany, 1989.

Hassig, B.E. and T.D. Davis, "A Historical Evaluation of Adventitious Rooting Research to 1993," *Biology of Adventitious Root Formation*, Basic Life Sciences, vol. 62, Plenum Press, 1994.

Howard, B.H., "Manipulating Rooting Potential in Stockplants Before Collecting Cuttings," *Biology of Advnetitious Root Formation*, Basic Life Sciences, vol. 62, Plenum Press, 1994.

Lloyd, G. and B. H. McCown. 1980. Commercially-feasible micropropagation of mountain laurel, *Kalmia Latifolia*, by use of shoot-tip culture. Somb. Proc. International Plant Prop. Soc. 30: 421–427.

Ritchie, G.A., "Commercial Application of Adventitious Rooting to Forestry", *Biology of Adventitious Root formation*, in Basic Life Sciences, vol. 62, Plenum Press, 1994.

Stein & Fortin, "Pattern of root initiation by an ectomycorrhizal fungus on hypocotyl cuttings of *Larix laricina*", Canadian Journal of Botany, 1990.

Bassil et al (1991) Hort Science 26 (8):1058–1060.

```
   1 AACTTGAGAG TTTNATCCTG GCTCAGAACG AACGCTNGCG GCATGCCTAA
  51 CACATGCAAG TCGAACGAGA CCTTCGGGTC TAGTGGCGCA CGGGTGCGTR
 101 ACGCGTGGGA ATCTGCCCTT GGGTTCGGAA TAACTCGCCG AAAGGCGTGC
 151 TAATACCGGA TGATGTCGTA AGACCAAAGA TTTATCGCCC AGGGATGAGC
 201 CCGCGTAAGA TTAGCTAGTT GGTGAGGTAA AGGCTCACCA AGGCGACGAT
 251 CTTTAGCTGG TCTGAGAGGA TGATCAGCCA CACTGGGACT GAGACACGGC
 301 CCAGACTCCT ACGGGAGGCA GCAGTGGGGA ATATTGGACA ATGGGCGAAA
 351 GCCTGATCCA GCAATGCCGC GTGAGTGATG AAGGCCTTAG GGTTGTAAAG
 401 CTCTTTTACC CGGGATGATA ATGACAGTAC CGGGAGAATA AGCTCCGGCT
 451 AACTCCGTGC CAGCAGCCGC GGTAATACGG AGGGAGCTAG CGTTGTTCGG
 501 AATTACTGGG CGTAAAGCGC ACGTAGGCGG CTTTGTAAGT CAGAGGTGAA
 551 AGCCTGGAGC TCAACTCCAG AACTGCCTTT GAGACTGCAT CGCTTGAATC
 601 CAGGAGAGGT GAGTGGAATT CCGAGTGTAG AGGTGAAATT CGTAGATATT
 651 CGGAAGAACA CCAGTGGCGA AGGCGGCTCA CTGGACTGGT ATTGACGCTG
 701 AGGTGCGAAA GCGTGGGGAG CAAACAGGAT TAGATACCCT GGTAGTCCAC
 751 GCCGTAAACG ATGATAACTA GCTGTCCGGG CACTTGGTGC TTGGGTGGCG
 801 CAGCTAACGC ATTAAGTTAT CCGCCTGGGG AGTACGGTCG CAAGATTAAA
 851 ACTCAAAGGA ATTGACGGGG GCCTGCACAA GCGGTGGAGC ATGTGGTTTA
 901 ATTCGAAGNA ACGCGCAGAA CCTTACCAGC GTTTGACATG TCCGGACGAT
 951 TTCCAGAGAT GGATCTCTTC CCTTCGGGGA CTGGAACACA GGTGCTGCAT
1001 GGCTGTCGTN AGCTCGTGTC GTGAGATGTT GGGTTAAGTC CCGCAACGAG
1051 CGCAACCCTC GCCNNTAGTT ACCATCATTT AGTTGGGGAC TCTAAAGGAA
1101 CCGCCGGTGA TAAGCCGGAG GAAGGTGGGG ATGACGTCAA GTCCTCATGG
1151 CCCTTACGCG CTGGGCTACA CACGTGCTAC AATGGCGGTG ACAGTGGGCA
1201 GCAAACTCGC GAGAGTGCGC TAATCTCCAA AAGCCGTCTC AGTTCGGATT
1251 GTTCTCTGCA ACTCGAGAGC ATGAAGGCGG AATCGCTAGT AATCGCGGAT
1301 CAGCATGCCG CGGTGAATAC GTTCCCAGGC NTTGTACACA CCGCCCGTCA
1351 CACCATGGGA GTTGGGTTCA CCCGAAGGCG TTGCGCTAAC TCGCAAGAGA
1401 GGCAGGCGAC CACGGTGGGC TTAGC
```

*FIG. 4*

| | |
|---|---|
| 1 | GAACGAACGC TGGCGGCATG CCTAACACAT GCAAGTCGAA CGAAGGCTTC |
| 51 | GGCCTTAGTG GCGCACGGGT GCGTAACGCG TGGGAATCTG CCCTTAGGTT |
| 101 | CGGAATAACA GCTGGAAACG CTGCTAATA CCGGATGATA TCGCGAGATC |
| 151 | AAAGATTTAT CGCCTGAGGA TGAGCCCGCG TTGGATTAGG TAGTTGGTGG |
| 201 | GGTAAAGGCC TACCAAGCCG ACGATCCATA GCTGGTCTGA GAGGATGATC |
| 251 | AGCCACACTG GACTGAGAC ACGGCCCAGA CTCCTACGGG AGGCAGCAGT |
| 301 | GGGGAATATT GGACAATGGG CGAAAGCCTG ATCCAGCAAT GCCGCGTGAG |
| 351 | TGATGAAGGC CCTAGGGTTG TAAAGCTCTT TTACCCGGGA AGATAATGAC |
| 401 | TGTACCGGGA GAATAAGCCC CGGCTAACTC CGTGCCAGCA GCCGCGGTAA |
| 451 | TACGGAGGGG CTAGCGTTG TTCGGAATTA CTGGGCGTAA AGCGCACGTA |
| 501 | GGCGGCTTTG TAAGTCAGAG GTGAAAGCCT GGAGCTCAAC TCCAGAACTG |
| 551 | CCTTTGAGAC TGCATCGCTT GAATCCAGGA GAGGTCAGTG GAATTCCGAG |
| 601 | TGTAGAGGTG AAATTCGTAG ATATTCGGAA GAACACCAGT GGCGAAGGCG |
| 651 | GCTGACTGGA CTGGTATTGA CGCTGAGGTG CGAAAGCGTG GGGAGCAAAC |
| 701 | AGGATTAGAT ACCCTGGTAG TCCACGCCGT AAACGATGAT AACTAGCTGT |
| 751 | CCGGGCACTT GGTGCTTGGG TGGCGCACGT AACGCATTAA GTTATCCGCC |
| 801 | TGGGGAGTAC GGCCGCAAGG TTAAAACTCA AGGAATTGA CGGGGGCCTG |
| 851 | CACAAGCGGT GGAGCATGTG GTTTAATTCG AAGCAACGCG CAGAACCTTA |
| 901 | CCAGCGTTTG ACATGGTAGG ACGACTTCCA GAGATGGATT TCTTCTTCGG |
| 951 | GGACCTACAC ACAGGTGCTG CATGGCTGTC GTCAGCTCGT GTCGTGAGAT |
| 1001 | GTTGGGTTAA GTCCCGCAAC GAGCGCAACC CTCGCCTTTA GTTACCATCA |
| 1051 | TTTGGTTGGG TACTCTAAAG GANACCGCCG GTGATAAGCC GGAGGAAGGT |
| 1101 | GGGGATGACG CCAAGTCCTC ATGGCCCTTA CGCGCTGGGC TACACACGTG |
| 1151 | CTACAATGGC AACTACAGTG GGCAGCGACC CTGCGAGGGC GAGCTAATCC |
| 1201 | CCAAAAGTTG TCTCAGTTCG GATTGTTCTC TGCAACTCGA GAGCATGAAG |
| 1251 | GCGGAATCGC TAGTAATCGC GGATCAGCAT GCCGCGGTGA ATACGTTCCC |
| 1301 | AGGCCTTGTA CACACCGCCC GTCACACCAT GGGAGTTGGA TTCACCCGAA |
| 1351 | GGCGTTGCGC CAACCTAGCA ATAGGAAGCA GGCGACCACG GTGGGTTCAG |
| 1401 | CGACTGGGGT GAAGTCGTAA CAAGGTAGCC GTAGGGGAAC CTGCGG |

*FIG. 5*

NAAACTTGAG AGTTTGATCC TGGCTCAGAA CGAACGCTAG CGGCATGCCT
AACACATGCA AGTCGAACGA AGGCTTCGGC CNNAGTGGCG CACGGGTGCG
TAACGCGTGG GAATCTGCCC TTAGGTTCGG AATAACAGCT GGAAACGGCT
GCTAATACCG GATGATATCG CGAGATCAAA GATTTATCGC CTGAGGATGA
GCCCGCGTTG GATTAGGTAG TTGGTGGGGT AAAGGCCTAC CAAGCCGACG
ATCCATAGCT AGTCTGAGAG GATGATCAGC CACACTGGGA CTGAGACACG
GCCNAGACTN CNACGGGAGG CAGCAGTGGG GAATATTGGA CAATGGGCGA
AAGCCTGATC CAGCAATGCC GCGTGAGTGA TGAAGGCCNT AGGGTTGTAA
AGCTNTTTTA CCCGGGAAGA TAATGACTGT ACCGGGAGAA TAAGCCCCGG
CTAACTCCGT GCCAGCAGCC NCGGTAATAC GGAGGGGGCN AGCGTTGTTC
GGAATTACTG GGCGTAAAGC GCACGTAGGC GGCNTTGTAA GTCAGAGGTG
AAAGCCTGGA GCTCAACTCC AGAACTGCCT TTGAGACTGC ATCGCTTGAA
TCCAGGAGAG GTCAGTGGAA TTCCGAGTGT AGAGGTGAAA TTCGTAGATA
TTCGGAAGAA CACCAGTGGC GAAGGCGGCN GACTGGACTG GNATTGACGC
TGAGGTGCNN AAGCGTGGGG AGCAAACAGG ATTAGATACC CTGGTAGTCC
ACGCCGTAAA CGATGATAAC TAGCTGTCCG GNCACTTGGT GCTTGGGTGG
CGCAGCTAAC GCATTAAGTT ATCCGCCTGG GGAGTACGGC CGCAAGGTTA
AAACTCAAAG GAATTGACGG GGGCCTGCAC AAGCGGTGGA GCATGTGGTT
TAATTCGAAN NAACGCGCAG AACCTTACCA GCGTTTGACA TGGTAGGACG
ACTTCCAGAG ATGGATTTCT TCCCTTCGGG GACCTACACA CAGGTGCTGC
ATGGCTGTCG TCAGCTCGTG TCGTGAGATG TTGGGTTAAG TCCCGCAACG
AGCGCAACCC TCGCCNTTAG TTACCATCAT TTGGTTGGGT ACTCTAAAGG
AACCGCCGGT GATAAGCNGG AGGAAGGTGG GGATGACGTC AAGTCCTCAT
GGCCCTTACG CGCTGGGCTA CACACGTGCT ACAATGGCAA CTACAGTGGG
CAGCGACCCT GCGAGGGCGA GCTAATCCCC AAAAGTTGTC TCAGTTCGGA
TTGTTCTCTG CAACTCGAGA GCATGAAGGC GGAATCGCTA GTAATCGCGG
ATCAGCATGC CGCGGTGAAT ACGTTCCCAG GCTTTGTACA CACCGCNCGT
CACACCATGG GAGTTGGATT CACCCGAAGG CGTTGCGCCA ACCTAGCAAT
AGGAAGCAGG CGACCACGGT GGGTTCAGCG ACTGGGG... ..........
.......... .......... .......... .......... ...

*FIG. 6*

LINE UP OF RSB (Rsb16saa), CAULOBACTER SUBVIBRIOIDES (Ccrrrnaa),
AVOBATERIUM DEVORANS (Fdevod) AND SPHINGOMONAS PAUCIMOBILIS (Spaucim).
OLD FACE NUCLEOTIDES INDICATE SITES OF MISMATCH.

```
           1                                                              50
Rsb16saa         AG AGTTTGATCA TGGCTCAGAA TGAACGCTGG CGGCATGCCT
Ccrrrnaa    AACTTGAG AGTTTNATCC TGGCTCAGAA CGAACGCTNG CGGCATGCCT
  Fdevod  NAAACTTGAG AGTTTGATCC TGGCTCAGAA CGAACGCTAG CGGCATGCCT
  Spaucim                   GAA CGAACGCTGG CGGCATGCCT 51                                                            100
Rsb16saa   AACACATGCA AGTCGAACGA AGGCTTCGGC CTTAGTGGCG CACGGGTGGC
Ccrrrnaa   AACACATGCA AGTCGAACGA GACCTTCGGG TCTAGTGGCG CACGGGTGCG
  Fdevod   AACACATGCA AGTCGAACGA AGGCTTCGGC CNNAGTGGCG CACGGGTGCG
  Spaucim  AACACATGCA AGTCGAACGA AGGCTTCGGC CTTAGTGGCG CACGGGTGCG 101                                                           250
Rsb16saa   TAACGCGTGG GAATCTGCCC TCAGGTTCGG AATAACAGCG ACAAATTGCT
Ccrrrnaa   TRACGCGTGG GAATCTGCCC TTGGGTTCGG AATAACTCGC CGAAAGGCGT
  Fdevod   TAACGCGTGG GAATCTGCCC TTAGGTTCGG AATAACAGCT GGAAACGGCT
  Spaucim  TAACGCGTGG GAATCTGCCC TTAGGTTCGG AATAACAGCT GGAAACGGCT 151                                                           300
Rsb16saa   GCTAATACCG GATGATATCG CGAGATCAAA GATTTATCGC CTGAGGATGA
Ccrrrnaa   CGTAATACCG GATGATGTCG TAAGACCAAA GATTTATCGC CCAGGGATGA
  Fdevod   GCTAATACCG GATGATATCG CGAGATCAAA GATTTATCGC CTGAGGATGA
  Spaucim  GCTAATACCG GATGATATCG CGAGATCAAA GATTTATCGC CTGAGGATGA 201                                                           350
Rsb16saa   GCCCGCGTAG GATTAGCTAG TTGGTGTGGT AAAGGCGCAC CAAGGCGACG
Ccrrrnaa   GCCCGCGTAA GATTAGCTAG TTGGTGAGGT AAAGGCTCAC CAAGGCGACG
  Fdevod   GCCCGCGTTG GATTAGGTAG TTGGTGGGGT AAAGGCCTAC CAAGCCGACG
  Spaucim  GCCCGCGTTG GATTAGGTAG TTGGTGGGGT AAAGGCCTAC CAAGCCGACG 251                                                           300
Rsb16saa   ATCCTTAGCT GGTCTGAGAG GATGATCAGC CACACTGGGA CTGAGACACG
Ccrrrnaa   ATCTTTAGCT GGTCTGAGAG GATGATCAGC CACACTGGGA CTGAGACACG
  Fdevod   ATCCATAGCT AGTCTGAGAG GATGATCAGC CACACTGGGA CTGAGACACG
  Spaucim  ATCCATAGCT GGTCTGAGAG GATGATCAGC CACACTGGGA CTGAGACACG 301                                                           350
Rsb16saa   GCCCAGACTC CTACGGGAGG CAGCAGTGGG GAATATTGGA CAATGGGCGA
Ccrrrnaa   GCCCAGACTC CTACGGGAGG CAGCAGTGGG GAATATTGGA CAATGGGCGA
  Fdevod   GCCNAGACTN CNACGGGAGG CAGCAGTGGG GAATATTGGA CAATGGGCGA
  Spaucim  GCCCAGACTC CTACGGGAGG CAGCAGTGGG GAATATTGGA CAATGGGCGA 351                                                           400
Rsb16saa   AAGCCTGATC CAGCAATGCC GCGTGAGTGA TGAAGGCCTT AGGGTTGTAA
Ccrrrnaa   AAGCCTGATC CAGCAATGCC GCGTGAGTGA TGAAGGCCTT AGGGTTGTAA
  Fdevod   AAGCCTGATC CAGCAATGCC GCGTGAGTGA TGAAGGCCNT AGGGTTGTAA
  Spaucim  AAGCCTGATC CAGCAATGCC GCGTGAGTGA TGAAGGCCCT AGGGTTGTAA
```

FIG. 7

| FIG. 7A |
| FIG. 7B |
| FIG. 7C |
| FIG. 7D |

FIG. 7A

```
              401                                                             450
Rsb16saa   AGCTCTTTTA CCCGGGATGA TAATGACAGT ACCGGGAGAA TAAGCTCCGG
Ccrrrnaa   AGCTCTTTTA CCCGGGATGA TAATGACAGT ACCGGGAGAA TAAGCTCCGG
 Fdevod    AGCTNTTTTA CCCGGGAAGA TAATGACTGT ACCGGGAGAA TAAGCCCCGG
 Spaucim   AGCTCTTTTA CCCGGGAAGA TAATGACTGT ACCGGGAGAA TAAGCCCCGG 451                                                             500
Rsb16saa   CTAACTCCGT GCCAGCAGCC GCGGTAATAC GGAGGGAGCT AGCGTTATTC
Ccrrrnaa   CTAACTCCGT GCCAGCAGCC GCGGTAATAC GGAGGGAGCT AGCGTTGTTC
 Fdevod    CTAACTCCGT GCCAGCAGCC NCGGTAATAC GGAGGGGGCN AGCGTTGTTC
 Spaucim   CTAACTCCGT GCCAGCAGCC GCGGTAATAC GGAGGGGGCT AGCGTTGTTC 501                                                             500
Rsb16saa   GGAATTACTG GGCGTAAAGC GCACGTAGGC GGCTTTGTAA GTTAGAGGTG
Ccrrrnaa   GGAATTACTG GGCGTAAAGC GCAGCTAGGC GGCTTTGTAA GCTAGAGGTG
 Fdevod    GGAATTACTG GGCGTAAAGC GCACGTAGGC GGCNTTGTAA GTCAGAGGTG
 Spaucim   GGAATTACTG GGCGTAAAGC GCACGTAGGC GGCTTTGTAA GTCAGAGGTG 551                                                             600
Rsb16saa   AAAGCCTGGA GCTCAACTCC AGAATTGCCT TTAAGACTGC ATCGCTTGAA
Ccrrrnaa   AAAGCCTGGA GCTCAACTCC AGAACTGCCT TTGAGACTGC ATCGCTTGAA
 Fdevod    AAAGCCTGGA GCTCAACTCC AGAACTGCCT TTGAGACTGC ATCGCTTGAA
 Spaucim   AAAGCCTGGA GCTCAACTCC AGAACTGCCT TTGAGACTGC ATCGCTTGAA 601                                                             650
Rsb16saa   TCCAGGAGAG GTGAGTGGAA TTCCGAGTGT AGAGGTGAAA TTCGTAGATA
Ccrrrnaa   TCCAGGAGAG GTGAGTGGAA TTCCGAGTGT AGAGGTGAAA TTCGTAGATA
 Fdevod    TCCAGGAGAG GTCAGTGGAA TTCCGAGTGT AGAGGTGAAA TTCGTAGATA
 Spaucim   TCCAGGAGAG GTCAGTGGAA TTCCGAGTGT AGAGGTGAAA TTCGTAGATA 651                                                             700
Rsb16saa   TTCGGAAGAA CACCAGTGGC GAAGGCGGCT CACTGGACTG GTATTGACGC
Ccrrrnaa   TTCGGAAGAA CACCAGTGGC GAAGGCGGCT CACTGGACTG GTATTGACGC
 Fdevod    TTCGGAAGAA CACCAGTGGC GAAGGCGGCN GACTGGACTG GNATTGACGC
 Spaucim   TTCGGAAGAA CACCAGTGGC GAAGGCGGCT GACTGGACTG GTATTGACGC 701                                                             750
Rsb16saa   TGAGGTGCGA AAGCGTGGGG AGCAAACAGG ATTAGATACC CTGGTAGTCC
Ccrrrnaa   TGAGGTGCGA AAGCGTGGGG AGCAAACAGG ATTAGATACC CTGGTAGTCC
 Fdevod    TGAGGTGCNN AAGGCTGGGG AGCAAACAGG ATTAGATACC CTGGTAGTCC
 Spaucim   TGAGGTGCGA AAGCGTGGGG AGCAAACAGG ATTAGATACC CTGGTAGTCC 751                                                             800
Rsb16saa   ACGCCGTAAA CGATGATAAC TAGCTGTCGG GGCTCTTAGA GCTTCGGTGG
Ccrrrnaa   ACGCCGTAAA CGATGATAAC TAGCTGTCCG GGCACTTGGT GCTTGGGTGG
 Fdevod    ACGCCGTAAA CGATGATAAC TAGCTGTCCG GNCACTTGGT GCTTGGGTGG
 Spaucim   ACGCCGTAAA CGATGATAAC TAGCTGTCCG GGCACTTGGT GCTTGGGTGG 801                                                             850
Rsb16saa   CGCACGTAAC GCATTAAGTT ATCCGCCTGG GGAGTACGGC CGCAAGGTTA
Ccrrrnaa   CGCAGCTAAC GCATTAAGTT ATCCGCCTGG GGAGTACGGT CGCAAGATTA
 Fdevod    CGCAGCTAAC GCATTAAGTT ATCCGCCTGG GGAGTACGGC CGCAAGGTTA
 Spaucim   CGCACGTAAC GCATTAAGTT ATCCGCCTGG GGAGTACGGC CGCAAGGTTA
```

*FIG. 7B*

```
              851                                                         900
Rsb16saa  AAACTCAAAT GAATTGACGG GGGCCTGCAC AAGCGGTGGA GCATGTGGTT
Ccrrrnaa  AAACTCAAAG GAATTGACGG GGGCCTGCAC AAGCGGTGGA GCATGTGGTT
  Fdevod  AAACTCAAAG GAATTGACGG GGGCCTGCAC AAGCGGTGGA GCATGTGGTT
 Spaucim  AAACTCAAAG GAATTGACGG GGGCCTGCAC AAGCGGTGGA GCATGTGGTT 901                                                         950
Rsb16saa  TAATTCGAAG CAACGCGCAG AACCTTACCA GCGTTTGACA TGTCCGGACG
Ccrrrnaa  TAATTCGAAG NAACGCGCAG AACCTTACCA GCGTTTGACA TGTCCGGACG
  Fdevod  TAATTCGAAN NAACGCGCAG AACCTTACCA GCGTTTGACA TGGTAGGACG
 Spaucim  TAATTCGAAG CAACGCGCAG AACCTTACCA GCGTTTGACA TGGTAGGACG 951                                                        1000
Rsb16saa  ATTTCGGGAG ACCGATCTCT TCCCTTCGGG GACTGGAACA CAGGTGCTGC
Ccrrrnaa  ATTTCCAGAG ATGGATCTCT TCCCTTCGGG GACTGGAACA CAGGTGCTGC
  Fdevod  ACTTCCAGAG ATGGATTTCT TCCCTTCGGG GACCTACACA CAGGTGCTGC
 Spaucim  ACTTCCAGAG ATGGATTTCT TCXXTTCGGG GACCTACACA CAGGTGCTGC 1001                                                        1050
Rsb16saa  ATGGCTGTCG TCAGCTCGTG TCGTGAGATG TTGGGTTAAG TCCCGCAACG
Ccrrrnaa  ATGGCTGTCG TNAGCTCGTG TCGTGAGATG TTGGGTTAAG TCCCGCAACG
  Fdevod  ATGGCTGTCG TCAGCTCGTG TCGGTAGATG TTGGGTTAAG TCCCGCAACG
 Spaucim  ATGGCTGTCG TCAGCTCGTG TCGTGAGATG TTGGGTTAAG TGGCGCAACG 1051                                                        1100
Rsb16saa  AGCGCAACCC TCGTCCTTAG TTGCCATCAT TTAGTTGGGC ACTCTAAGGA
Ccrrrnaa  AGCGCAACCC TCGCCNNTAG TTACCATCAT TTAGTTGGGG ACTCTAAAGG
  Fdevod  AGCGCAACCC TCGCCNTTAG TTACCATCAT TTGGTTGGGT ACTCTAAAGG
 Spaucim  AGCGCAACCC TCGCCTTTAG TTACCATCAT TTGGTTGGGT ACTCTAAAGG 1101                                                        1150
Rsb16saa  AAXCCGCCGG TGATAAGCCG GAGGAAGGTG GGGATGACGT CAAGTCCTCA
Ccrrrnaa  AAXCCGCCGG TGATAAGCCG GAGGAAGGTG GGGATGACGT CAAGTCCTCA
  Fdevod  AAXCCGCCGG TGATAAGCNG GAGGAAGGTG GGGATGACGT CAAGTCCTCA
 Spaucim  ANACCGCCGG TGATAAGCCG GAGGAAGGTG GGGATGACGC CAAGTCCTCA 1151                                                        1200
Rsb16saa  TGGCCCTTAC GCGCTGGGCT ACACACGTGC TACAATGGCG GTGACAGTGG
Ccrrrnaa  TGGCCCTTAC GCGCTGGGCT ACACACGTGC TACAATGGCG GTGACAGTGG
  Fdevod  TGGCCCTTAC GCGCTGGGCT ACACACGTGC TACAATGGCA ACTACAGTGG
 Spaucim  TGGCCCTTAC GCGCTGGGCT ACACACGTGC TACAATGGCA ACTACAGTGG 1201                                                        1250
Rsb16saa  GCAGCAATCT CGCAAGGGTG AGCTAATCTC CAAAAGCCGT CTCAGTTCGG
Ccrrrnaa  GCAGCAAACT CGCGAGAGTG CGCTAATCTC CAAAAGCCGT CTCAGTTCGG
  Fdevod  GCAGCGACCC TGCGAGGGCG AGCTAATCCC CAAAAGTTGT CTCAGTTCGG
 Spaucim  GCACGCACCC TGCGAGGGCG AGCTAATCCC CAAAAGTTGT CTCAGTTCGG 1251                                                        1300
Rsb16saa  ATTGTTCTCT GCAACTCGAG AGCATGAAGG CGGAATCGCT AGTAATCGCG
Ccrrrnaa  ATTGTTCTCT GCAACTCGAG AGCATGAAGG CGGAATCGCT AGTAATCGCG
  Fdevod  ATTGTTCTCT GCAACTCGAG AGCATGAAGG CGGAATCGCT AGTAATCGCG
 Spaucim  ATTGTTCTCT GCAACTCGAG AGCATGAAGG CGGAATCGCT AGTAATCGCG
```

*FIG. 7C*

```
           1301                                                 1350
Rsb16saa   GATCAGCATG CCGCGGTGAA TACGTTCCCA GGCCTTGTAC ACACCGCCCG
Ccrrrnaa   GATCAGCATG CCGCGGTGAA TACGTTCCCA GGCNTTGTAC ACACCGCCCG
  Fdevod   GATCAGCATG CCGCGGTGAA TACGTTCCCA GGCTTTGTAC ACACCGCNCG
 Spaucim   GATCAGCATG CCGCGGTGAA TACGTTCCCA GGCCTTGTAC ACACCGCCCG 1351                                                 1400
Rsb16saa   TCACACCATG GGAGTTGGAT TCACCCGAAG GCAGTGCGCT AACXXCGCAA
Ccrrrnaa   TCACACCATG GGAGTTGGGT TCACCCGAAG GCGTTGCGCT AACTXCGCAA
  Fdevod   TCACACCATG GGAGTTGGAT TCACCCGAAG GCGTTGCGCC AACCTAGCAA
 Spaucim   TCACACCATG GGAGTTGGAT TCACCCGAAG GCGTTGCGCC AACCTAGCAA 1401                                                 1450
Rsb16saa   XXGGAGGCAG CTGACCACGG TGGGTTCAGC GACTGGGGTG AAGTCGTAAC
Ccrrrnaa   XGAGAGGCAG GCGACCACGG TGGGCTTAGC
  Fdevod   TAGGAAGCAG GCGACCACGG TGGGTTCAGC GACTGGGG.. ..........
 Spaucim   TAGGAAGCAG GCGACCACGG TGGGTTCAGC GACTGGGGTG AAGTCGTAAC 1451                               1494
Rsb16saa   AAGGTAACC
  Fdevod   .......... .......... .......... ....
 Spaucim   AAGGTAGCCG TAGGGGAACC TGCGG
```

*FIG. 7D*

ONE OF TWO MOST PARSIMONIOUS TREES OBTAINED BY AN EXHAUSTIVE SEARCH ALGORITHM OF PAUP VERSION 3.0 USING R. SALEXIGENES AS AN OUTGROUP. THIS TREE HAS A LENGTH OF 427 STEPS, A CONSISTENCY INDEX OF 0.717 AND A RESCALED CONSISTENCY INDEX OF 0.493.

ROOT STIMULATING BACTERIA

This application is a continuation-in-part of U.S. patent application Ser. No. 08/249,901, filed on May 26, 1994.

BACKGROUND OF THE INVENTION

1. Field

This invention relates broadly to the field of plant growth and development, particularly to forestry. The invention relates to initiation and promotion of adventitious rooting in plants in general including woody plants, like evergreens, particularly in conifers and in deciduous trees.

This invention also relates to a novel strain of a microorganism which initiates adventitious rooting in plants. Further, the invention relates to a method of promoting adventitious rooting of plants, in particular by co-culturing nonpathogenic bacteria in plants. The invention also relates to a composition, which may but need not include the microorganism, which initiates adventitious rooting in plants and to a method for using the composition to promote rooting in plants.

The invention relates to various tree products, such evergreens obtained from the invention. The invention also relates to various other compositions described further below.

2. Description of the Prior Art

In the United States, forest propagation is primarily seedling based. However, growing seedlings is a slow, labor intensive process, requiring one year in greenhouses and up to four years in outdoor nurseries. Few forest trees, with the exception of poplars and willows and a few others, have ever been vegetatively propagated on a commercial scale. Furthermore, vegetative propagation of conifers, which makes up most of the West's timber supply, is relatively unheard of.

The need for efficient vegetative propagation of forest trees is not limited to the United States, but is world-wide. Japan plants nearly 30 million rooted suji cuttings annually. Europe likewise is seriously concerned about reforestation.

Many of the commercially important tree species, conifers or deciduous, have proven to be difficult to propagate vegetatively by current methods. These hard-to-root plants include the conifers such as pines, spruces, larches, e.g., Douglas fir. Stimulation of rooting has proved to be difficult in mature stocks in vitro cultures in several genera like Celtis, Ouercus, Sassafras, magnolias and conifers. The ability to promote the rooting of recalcitrant tree species, both juvenile and mature individuals, is expected to lead to, in accordance with the invention, the development of new plant products and new markets.

The need to promote rooting is not limited to evergreens like conifers, but applies also to other vegetative plants like deciduous trees, flowering and vegetable plants, and others. It is evident that any plant can benefit from promoting or accelerating of rooting. There is also an important need and commercial importance to promote the growing of plants, e.g., trees which are not so difficult to root, as this promotes an earlier or longer growth period.

In addition to forestry, vegetative propagation is used extensively in horticulture crops, including ornamentals, fruits, nuts, and vegetables. Floriculture is accomplished almost exclusively by cuttings. Many of the world's high carbohydrate vegetable crops, such as potato, yam, sweet potato, and cassava, are routinely asexually propagated.

The following U.S. patents relate to the problem of attempting to induce rooting or vegetative propagation in plants: U.S. Pat. Nos. 5,236,841, 4,353,184, 5,168,059, 5,240,839, 5,059,241, 5,229,114, 4,863,506 and 5,276,005. Of these, U.S. Pat. No. 5,229,114 deals with the use of bacteria to control root nodulation in leguminous plants. Others listed below deal with attempts to induce root formation with chemical molecules. All these patents are incorporated herein by reference.

Several methods have been attempted to stimulate rooting of plants. Dark preconditioning of shoots by covering with black tape has been shown to promote rooting. However, growing these shoots in less than ideal weather, such as in high humidity or during dull weather, results in necrosis and rotting, rather than rooting.

Chemicals, such as auxins, have been proposed to promote rooting of plants. Examples of auxins are indole-3-butyric acid (IBA), indole-3-acetic acid (IAA), and naphthalene acetic acid (NAA). Treatment of plants with rooting hormones frequently produces abnormal roots, which are thick, tubular, and stubby. See FIG. 1. Additionally, the stubby rooted plants, if they survive to grow normally, are delayed in their growth. The precise role of auxins in stimulation of rooting has not been accurately determined.

Other non-auxin hormones have been shown to have effects on adventitious rooting in plants. Cytokinins and gibberellins inhibit rooting. A method to induce adventitious budding consisting of repeated spray applications of trees with cytokinins, followed by treatment with auxins, has been described. U.S. Pat. No. 4,353,184 (Abo El-Nil). A method to promote somatic embryogenesis in tissue culture using repeated treatments with abscisic acid, a hormone believed to promote rooting through its antagonistic action to cytokinins and gibberellins, has been described. U.S. Pat. No. 5,236,841 (Gupta). None of these chemicals have been found to be fully satisfactory or have found acceptance on a commercial scale.

Different species of fungi have been described which produce auxins and other plant hormones and which may promote rooting by providing these hormones.

Stimulation of adventitious rooting in plants by co-culturing with bacteria has been described in many plant species. Adventitious roots formed and somatic embryos were regenerated from soybean (*Glycine max* L.) nodular calli induced by co-cultivation of cotyledonary explants with *Pseudomonas maltophilia*. However, pathologic effects of *P. maltophilia* were observed, the parent callus growth was inhibited or the callus died.

The bacteria, *Agrobacterium rhizogenes*, transforms the genome of its host plant which then carries the Ri gene of *A. rhizogenes*. Although transformed plants have increased root weight, they have decreased shoot weight when compared with normal non-transformed plants. The shoots produced from transformed plants are altered, and flowers are smaller compared to normal plants. Additionally, the root systems of plants infected with *A. rhizogenes* are altered, often to the extent that the altered root condition is referred to as hairy root disease. Although *A. rhizogenes* has been used effectively, although inconsistently, to promote rooting, it is uncertain to what extent the transformation of the host plant's genome can lead to deleterious effects.

Similarly, *Agrobacterium tumefaciens* induces rooting but causes crown gall disease.

It is evident that bacteria have not as yet proven satisfactory to promote root induction and growth of plants.

From this review of the literature and patents it is apparent that a world-wide serious need exists relating to propagation of plants, in general be it deciduous trees, ornamentals or crops, or in particular trees like conifers to promote initiation of adventitious rooting systems without causing pathology. This need has been addressed for many years. It is noteworthy that none of the solutions proposed have been found to be entirely satisfactory.

This invention contributes to solving this world-wide need, a need that is becoming increasingly serious because of industrialization and the awareness of the world's limited natural resources.

In view of the lack of success of the reported work in promoting healthy rooting systems in plants, in particular, with various bacterial systems, the findings, and success with bacteria in accordance with the invention are particularly unexpected.

The bacteria discovered in accordance with the invention have been designated as Root Stimulating Bacteria (RSB).

SUMMARY OF THE INVENTION

In accordance with the invention, a novel bacteria, belonging to a heretofore not identified species has been discovered. This bacteria, it has been found in accordance with the invention, stimulates and initiates adventitious rooting and/or promotes an increase in the number of roots in plants. The RSB has such an effect as described herein on plants in general whether deciduous or evergreen plants, e.g., trees. The described effect has been shown on trees whether or not they are relatively easy or difficult to root. The novel bacteria species which has been discovered does not only stimulate adventitious rooting in plants, but surprisingly also is not pathogenic to the target plant tissue.

The novel species of bacterium which has been discovered has been isolated and cultured. In accordance with the invention, when co-cultured under in vitro conditions with in vitro-produced microshoots of axillary origin or seedling-produced hypocotylary cuttings, the bacteria initiates adventitious rooting. Likewise, the bacteria was found to promote ex-vitro rooting of loblolly pine cuttings. The beneficial effect of the bacteria appears not to be specific as several species of conifers and non-coniferous plants have responded positively to the root inducing bacterial treatment. In accordance with the invention, subsequent root development observed from the plants exposed to the bacteria has been noted to be similar, if undistinguishable, to that found in young untreated seedling trees. Further, plants in accordance with the invention which have developed such rooting systems have developed secondary branching which is the precursor of a well-developed secondary fibrous root systems. In accordance with the invention, the plants with such stimulated adventitious rooting systems have been transferred to greenhouses and then to the outdoors where they have been growing normally.

An embodiment of the invention is a method for stimulating adventitious rooting in plants. The method comprises exposing a part of a plant, particularly a hypocotyl or the base of a microcutting of a plant, to a culture containing live bacteria of the novel RSB. The plant is then planted in a suitable growth medium, then, if desired as growth proceeds, is transferred to normal soil under greenhouse or other controlled environmental conditions and then field conditions where the plant has been observed to continue to grow normally. Particularly, the invention provides a method for such root development in conifers which are known to have considerable difficulty in developing such rooting systems. It has been further discovered that plants grown in medium extract which previously contained RSB and is free of the RSB, produce adventitious shoots and roots. This finding suggests that the presence of the RSB is not essential and that the RSB provides a molecule(s) which has the beneficial effects discussed above and/or stimulates the plant to provide or synthesize such a molecule(s) which has, directly or indirectly, such an effect.

The novel bacterium species has been identified to belong to a species that nests within a major branch of the α subdivision of the Proteobacteria showing the closest relationship to *Caulobacter subvibrioides*. The new bacteria species has been identified and classified by the now well accepted sequencing of the small subunit ribosomal RNA, namely the 16S rRNA. The phylogenetic analysis of this unique RSB bacterium has been based on the 16S rRNA sequence analysis. Sequence data information transferred and compared with an appropriate data bank (identified below) has shown that the sequence is unique.

Although the RSB is distinguished from other bacteria by its 16S rRNA transcribed from the nucleotide sequence further illustrated hereinafter, the invention is not limited to that particular sequence but includes RSBs which have the same or similar beneficial effect as the RSB disclosed herein and yet show variations in the nucleotide sequence(s).

Further embodiments of the invention include various media for culturing the RSB, plants, in particular conifers and deciduous trees, and parts thereof which have been developed in accordance with the invention.

Other embodiments of the invention will become apparent in the further detailed description of preferred and other embodiments of the invention.

The term "adventitious roots" is widely used to designate a root that arises either on an already lateralized root axis or at a site on the plant that is not itself a root (e.g., on a shoot or leaf).

Deposit Information

The new bacteria species of the invention (RSB) has been deposited under the terms of the Budapest Treaty at the American Type Culture Collection (ATCC), Rockville, Md., USA, on May 19, 1994, where it has been given accession No. ATCC 55580 under the designation RSB-1.

BRIEF DESCRIPTION OF THE FIGURES

FIG. 4 shows the 16S rRNA DNA base sequence of *Caulobacter subvibrioides*. Seq. I.D. No. 3.

FIG. 5 shows the 16S rRNA DNA base sequence of *Sphingomonas paucimobilis*. Seq. I.D. No. 4.

FIG. 6 shows the 16S rRNA DNA base sequence of *Flavobacterium devorans*. Seq. I.D. No. 5.

FIG. 7 shows the 16S rRNA DNA base sequence of RSB, Seq. I.d. No. 6, in comparison with that of *C. subvibrioides*, Seq. I.D. No. 3., *S. paucimobilis*, Seq. I.D. No. 4., and *F. devorans* Seq. I.D. No. 5.

DETAILED DESCRIPTION OF A PREFERRED EMBODIMENT OF THE INVENTION

Figure 1A:
FIG. 1 is a photograph showing the abnormal growth of roots induced by auxins.

In a preferred embodiment, the RSB were isolated from slash pine (Pinus elliottii) seedling explants cultured in vitro on charcoal containing modified Gresshoff and Doy medium. Isolation of the RSB was achieved as follows.

Slash pine in vitro cultures were rogued for any visible bacterial or fungal contamination. From this group of contaminated cultures, all tubes containing rooted explants were examined for some common feature/contaminant. It was observed that a great majority of rooted-contaminated cultures contained an easily recognized mustard-yellow contaminant that almost always was found to be visible around the base of the explant on the agar surface. Several tubes that seemed to contain this single contaminant were selected and a portion of the mustard-yellow colony was removed and subcultured initially by transfer to a non-contaminated culture tube containing a slash pine hypocotylary explant. Eventually RSB was found to grow vigorously on woody plant medium ("WPM") supplemented with 2% sucrose and with 0.2% casein hydrolysate ("enhanced" WPM). The pure culture line was established by repeated subculturing on "enhanced WPM" using an isolated colony as the source for the bacterial streak.

The RSB was grown on Difco™ Lowenstein-Jensen medium in deep culture tubes. Very rapid growth on both liquid and solid media was fostered when RSB was cultured on a modified WPM, supplemented with 2% sucrose as a source of sugar and 0.2% casein hydrolysate as a source of nitrogen and reduced carbon. Readily fermentable sugars other than sucrose and sources of amino acids or nitrogen and reduced carbon other than casein may be used in the medium. Cultures were incubated at 30° C. in dark. Subculturing was performed using a t-streak technique to obtain isolated culture at 1 to 2 week intervals. Liquid cultures of RSB were produced using identical medium and growth conditions with culture agitation on a rotary shaker (60 to 80 rpm).

A bank of the RSB was maintained in 15% glycerol at −80° C. Maintained in this way, a frozen living culture of RSB can be maintained for extended periods of time and can be packaged and shipped. An aliquot of this bacterial stock was used to inoculate a culture medium containing the above described woody plant medium. This medium was used as inoculum for further cultures and DNA extractions.

The RSB bacteria have been found to have the following characteristics.

(1) Growth on Various Nutrient Media

Table 1 below shows growth characteristics of RSB on various nutrient agar media.

TABLE 1

| GROWTH OF RSB ON VARIOUS MEDIA | |
| --- | --- |
| MEDIUM | GROWTH RESPONSE |
| NUTRIENT BROTH AGAR | POOR |
| TRYPTICASE SOY BROTH AGAR | POOR TO NO |

TABLE 1-continued

| GROWTH OF RSB ON VARIOUS MEDIA | |
| --- | --- |
| MEDIUM | GROWTH RESPONSE |
| LOWENSTEIN-JENSEN MEDIUM | MODERATE |
| ENHANCED WPM (SOLID & LIQUID) | GOOD |
| PEPTONE YEAST EXTRACT (LOW P) | MODERATE |
| LIQUID POTATO MEDIUM | GOOD |

(2) Physiological Characteristics

1) Temperature range permitting growth

Temperature permitting growth: 20°–35° C.

Optimum temperature for growth: 27°–30° C.

2) Nutritional requirements

In general, media rich in nutrients seem to inhibit growth. Most commercial media are designed for the culture of enteric bacteria found in human and other higher animals at pH levels much higher than RSB seems to be able to tolerate. RSB grows well at the pH of our plant culture medium pH 5.2 plus additional organic carbon and nitrogen in the form of 0.2% casein hydrolysate. Better growth might be seen in other media if they were adjusted to the lower 5.2 pH level.

3) Pigment formation: absorption spectra suggests the presence of carotenoids.

The RSB of the invention has been further identified and classified by its ribosomal sequence. Applicability of small subunit ribosomal RNA (16S rRNA) sequence for bacterial classification is now well accepted. Comparative analysis of the rRNA sequences from different sources reveals some stretches of highly conservative primary sequences and other sequences with a significant variability. The change in the variable portions of RNAs are a stable trait permitting the construction of consistent phylogenetic trees. These sequences permit identification of the RSB of the invention.

On the basis of the rRNA of the RSB, the RSB has been determined to be a member of the α subdivision of Proteobacteria. RSB bears a close relationship to members of nine different genera within the α branch of Proteobacteria, especially to Caulobacter subvibrioides, Flavobacterium devorans, and Sphingomonas paucimobilis. FIG. 4 shows the 16S rDNA sequence of C. subvibrioides. FIG. 5 shows the 16S rDNA sequence of S. paucimobilis. FIG. 6 shows the 16S rDNA sequence of F. devorans. Of these, based on 16S rDNA analyses, RSB is most closely related to, but different from, C. subvibrioides.

Figure 1B:
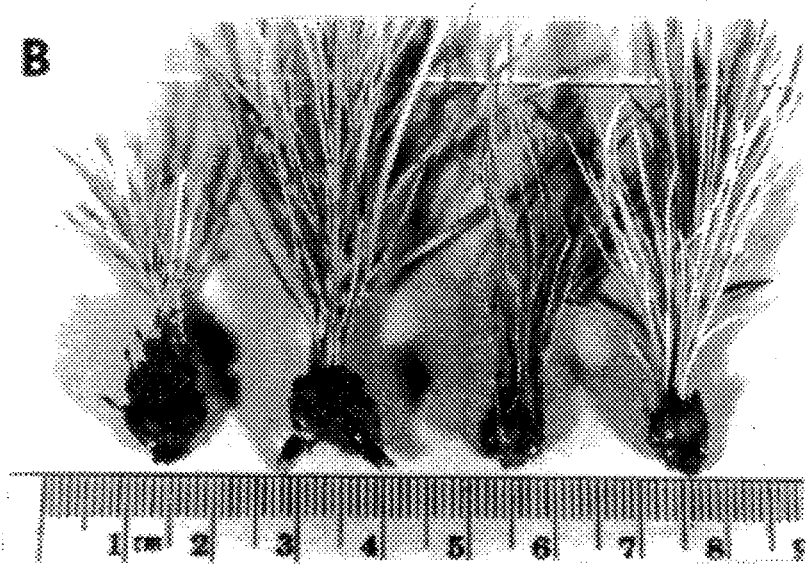
Figure 1C:
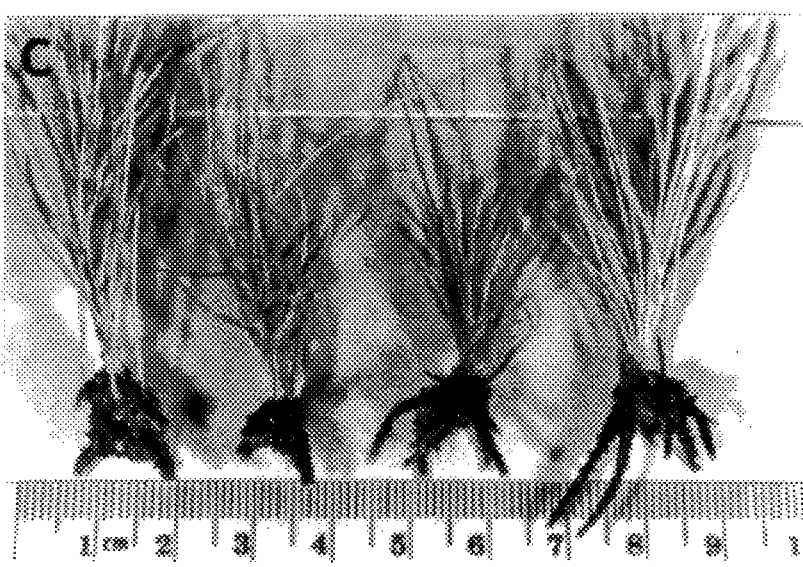

FIG. 1 is a photograph showing representative shoots from various treatments with plant hormones after 63 days in culture. At the top are control untreated shoots. In the center are shoots treated with 1.0 mg/L NAA and 0.1 mg/L BA. At the bottom are shoots treated with 0.5 mg/L NAA and 0.1 mg/L BA. The abnormal rooting produced by the auxin treatment is evident.

Figure 2:
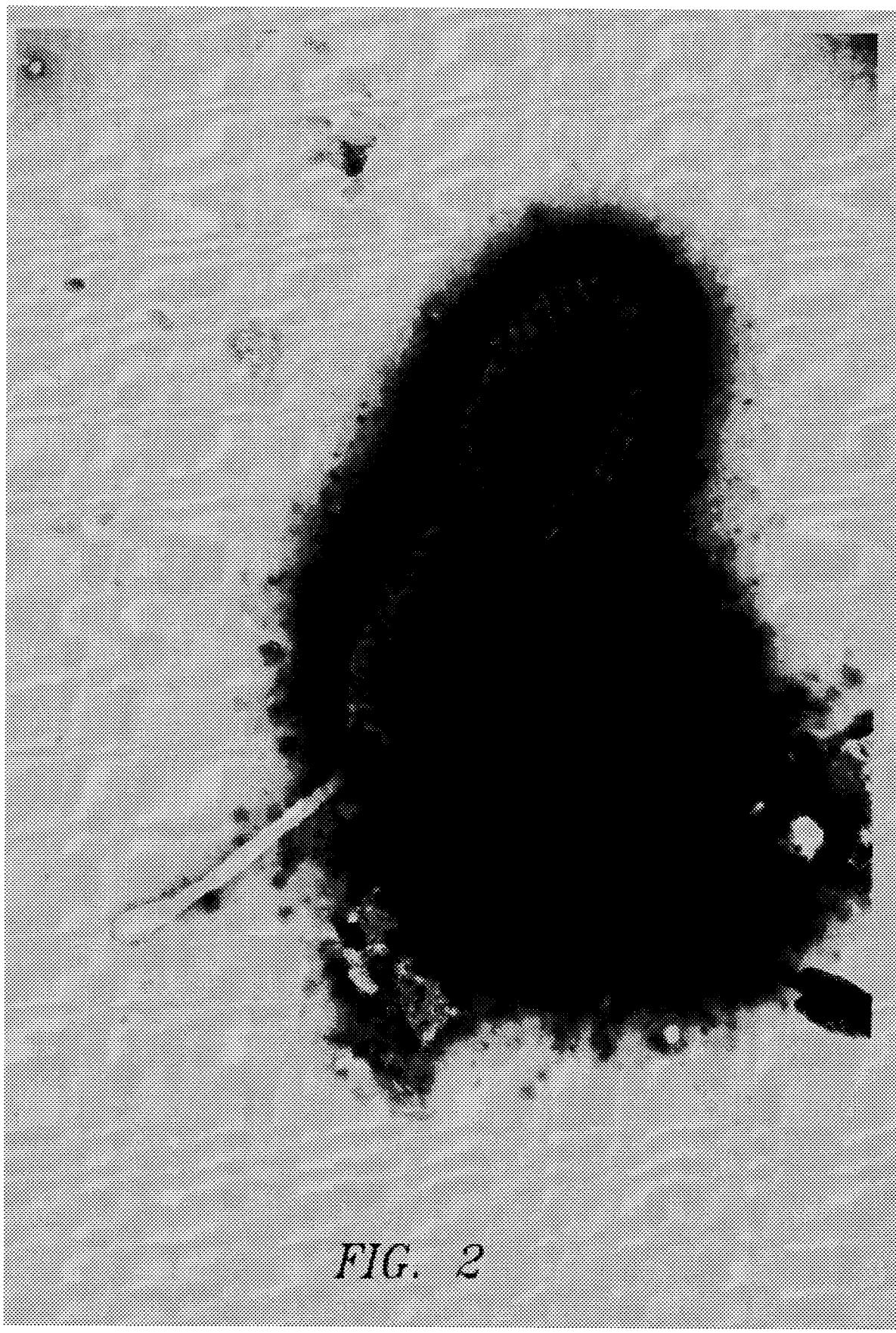
FIGS. 2–3 are microphotographs of the RSB bacteria.
Figure 3:

FIGS. 2 and 3 are microphotographs of the RSB. The cells are mostly rod-shaped, occasionally vibrioid or rarely fusiform, about 0.65 to 0.7 μm in length. Some cells were observed to be 3 to 4 times this average length. Cells were found to be occasionally stalked (ca. 70 nm in diameter and variable in length), and the polar stalk may be terminated by a holdfast (as described for the Caulobacter; Bergey's Manual of Systematic Bacteriology, 1984). Motile cells present have a singular polar flagellum. RSB is gram negative. Colonies are circular, convex, with a smooth margin, and glistening when actively growing. The color of actively growing colonies is a bright yellow, to mustard-yellow in slower growing or static colonies.

FIGS. 4, 5 and 6 show 16S rDNA sequences of the three bacteria which are phylogenetically closest to RSB, *C. subvibrioides, S. paucimobilis*, and *F. devorans*.

FIG. 7 shows a comparison of the DNA sequences of RSB and of the three closest bacteria, the non-homologous nucleotides being shown in bold.

Figure 8:
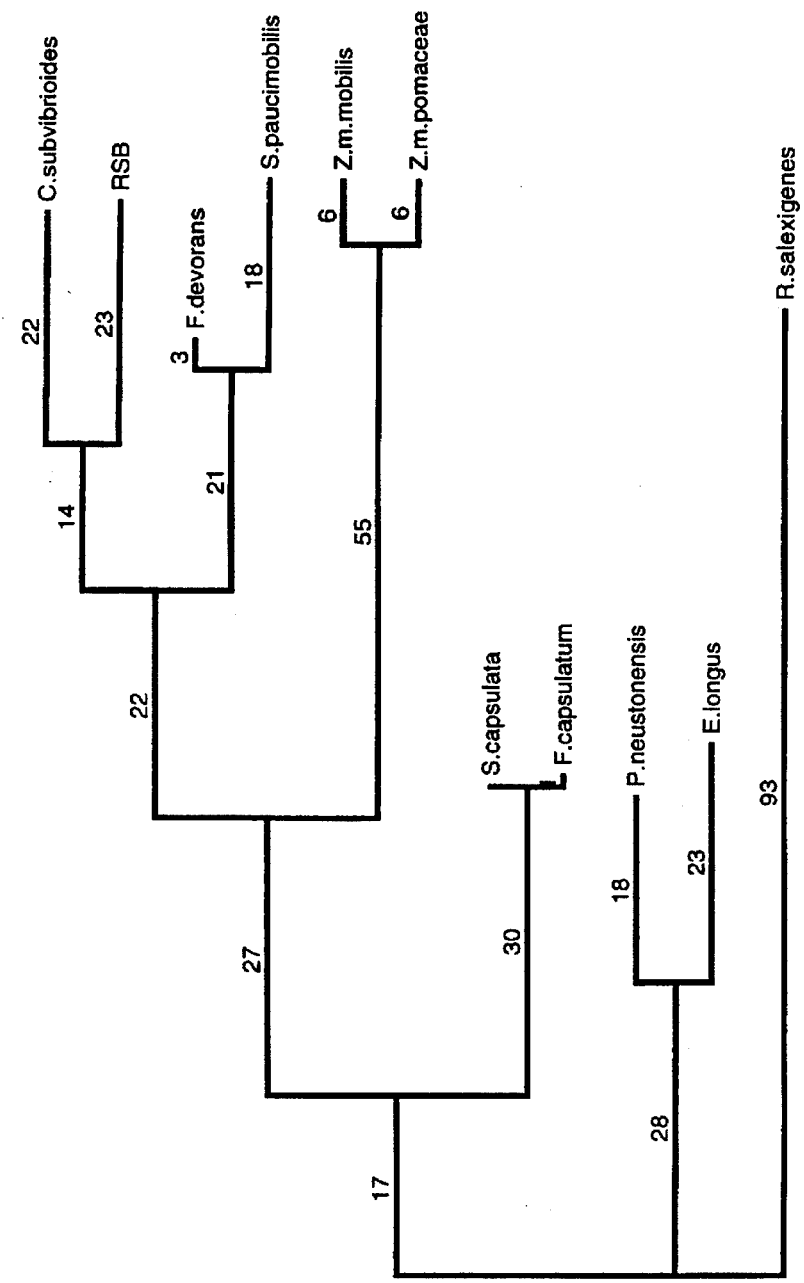
FIG. 8 shows one of the most parsimonious trees based on the analysis of 16S rRNA DNA sequence data of members of Proteobacteria.

FIG. 8 shows one of the two most parsimonious trees obtained by an exhaustive search algorithm of PAUP Version 3.0 using *Rhodospirillum salexigenes* as an outgroup. This tree has a length of 427 steps, a consistency index of 0.717 and a rescaled consistency index of 0.493. From this tree, the relationship of RSB to *C. subvibrioides, F. devorans* and *S. paucimobilis* is seen.

Figure 9:
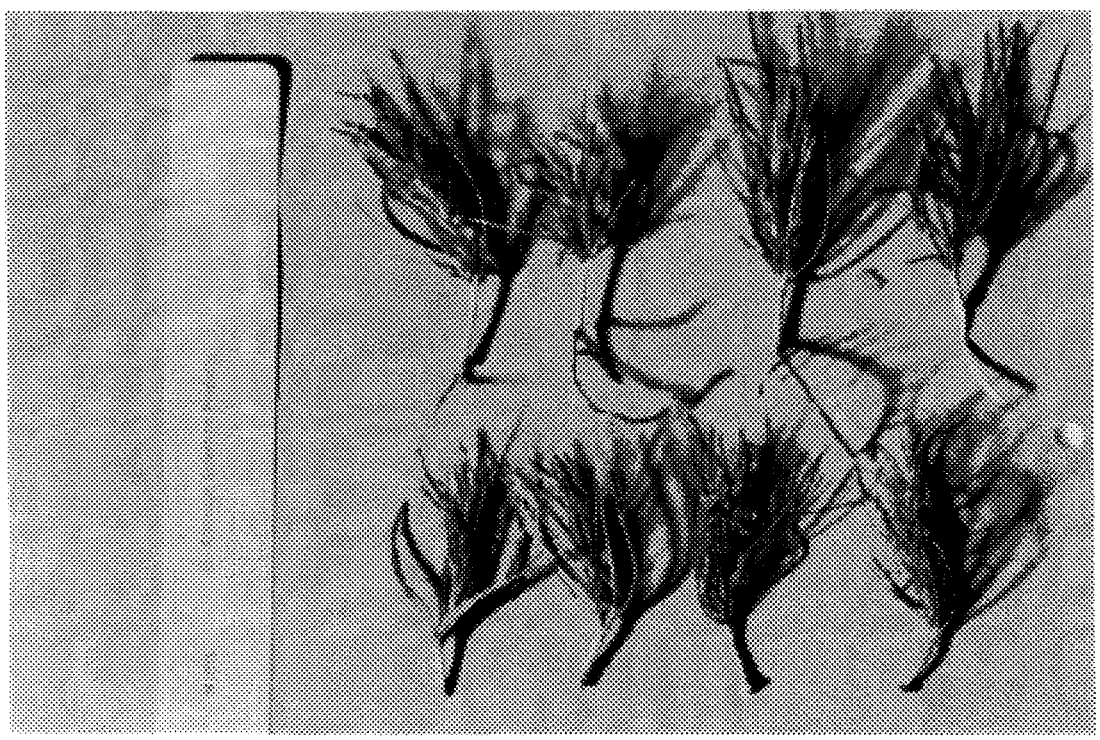
FIG. 9 is a photograph showing the comparison of rooting in RSB treated explants versus controls 7 weeks after treatment.

FIG. 9 shows the typical rooting patterns exhibited by white pine (*Pinus strobus*) hypocotylary explants after in vitro exposure to RSB. The top row shows RSB treated plants, the bottom row untreated controls.

Figure 10A:
FIG. 10 is a photograph showing the typical growth pattern in RSB treated explants of white pine versus controls.
Figure 10B:
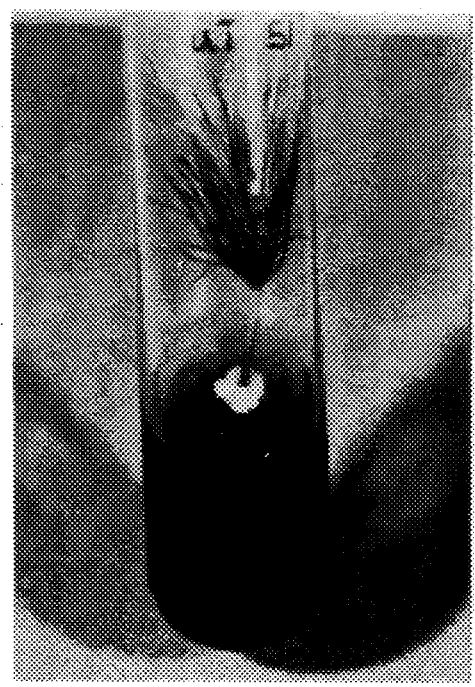

FIG. 10 shows adventitious rooting of white pine (*Pinus strobus*) hypocotylary explants as a result of exposure to RSB. Explants were obtained from seedlings grown in soil for 12 weeks. Significant levels of rooting were observed after 7 weeks exposure to the bacteria. The left side shows untreated control, the right side RSB treated.

Figure 11:
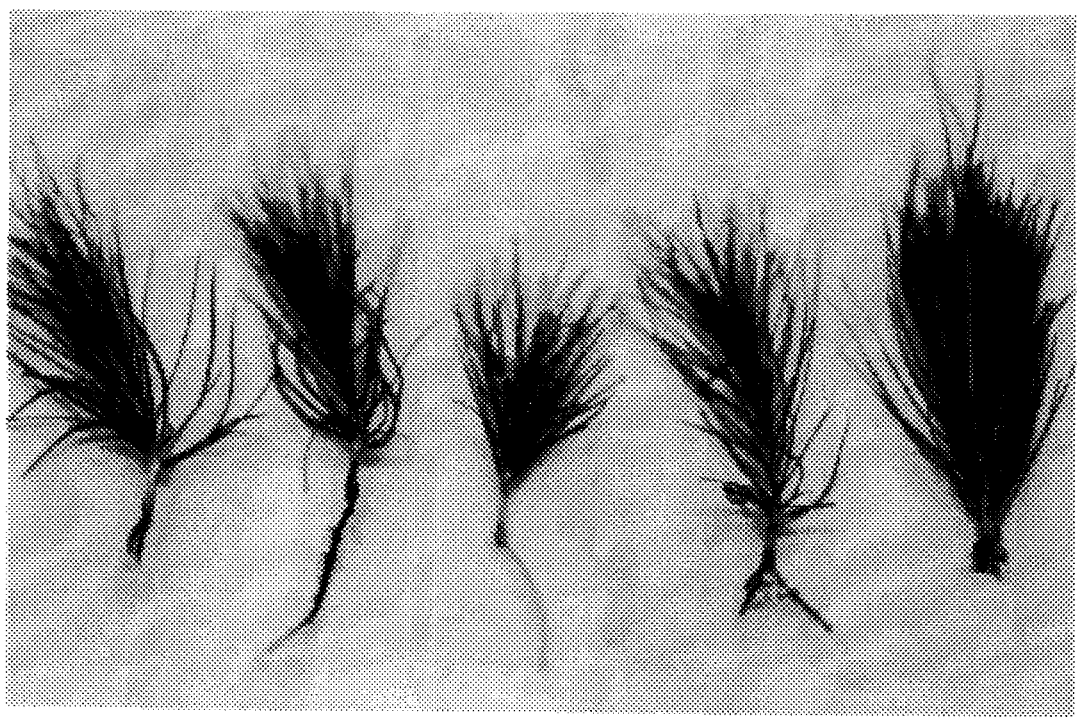
FIG. 11 is a photograph showing the production of primary and secondary root formation in slash pine explants 6 weeks after treatment with RSB.

FIG. 11 shows rooted slash pine (*Pinus elliottii*) hypocotylary explants after exposure to RSB under in vitro conditions. These explants were harvested from 24-week-old seedlings. The root development shown occurred after 6 weeks of incubation post-treatment with RSB.

Figure 12:
FIG. 12 shows a photograph of a rooted axillary bud plant grown in a green house and then transferred outside.

FIG. 12 shows a rooted axillary plant bud grown in a greenhouse and later transferred outside. The green upper part of the plant is due to growth out of doors.

The background effect of the RSB of the invention has been shown herein by a preferred embodiment on difficult to root conifers, such as loblolly pine, and deciduous trees, such as maple, magnolia, and *Casuarina spp.*, and flowering plants. These were selected as test models. Other conifers and plants likewise benefit from treatment with the RSB of the invention. Such conifers include the following shown in Table 2 below in which several illustrated species are identified.

It is anticipated that RSB will induce root formation in the following non-limiting examples of conifers (see Table 2):

TABLE 2

| Needle-leaf Conifers |
| --- |
| Pines |
| Eastern White Pine - *Pinus strobus* |
| Longleaf Pine - *Pinus palustris* |
| Loblolly Pine - *Pinus taeda* |
| Pond Pine - *Pinus serotina* |
| Pitch Pine - *Pinus rigida* |
| Red Pine - *Pinus resinosa* |
| Austrian Pine - *Pinus nigra* |
| Shortleaf Pine - *Pinus echinata* |
| Table Mountain Pine - *Pinus pungens* |
| Spruce Pine - *Pinus glabra* |
| Scotch Pine - *Pinus sylvestris* |
| Sand Pine - *Pinus clausa* |
| Virginia Pine - *Pinus virginiana* |
| Jack Pine - *Pinus banksiana* |
| Cedar-of-Lebanon - *Cedrus libani* |
| Larches |
| European Larch - *Larix decidua* |
| Tamarack - *Larix laricina* |
| Hemlocks |

TABLE 2-continued

| |
| --- |
| Carolina Hemlock - *Tsuga caroliniana* |
| Eastern Hemlock - *Tsuga canadensis* |
| Firs |
| Fraser Fir - *Abies fraseri* |
| Balsam Fir - *Abies balsamea* |
| Spruces |
| White Spruce - *Picea glauca* |
| Black Spruce - *Picea mariana* |
| Red Spruce - *Picea rubens* |
| Norway Spruce - *Picea abies* |
| Baldcypresses |
| Baldcypress - *Taxodium distichum* |
| Montezuma Baldcypress - *Taxodium mucronatum* |
| Yews |
| Florida Yew - *Taxus floridana* |
| Florida Torreya - *Torreya taxifolia* |
| Pacific Yew - *Taxus borevifolti* |
| Canadian Yew - *Taxus canadensis* |
| Scale-leaf Conifers |
| Cypresses |
| Oriental Arborvitae - *Thuja orientalis* |
| Sawara False-cypress - *Chamaecyparis pisifera* |
| Cedars |
| Northern White-cedar - *Thuja occidentalis* |
| Atlantic White-cedar - *Chamaecyparis thyoides* |
| Eastern Redcedar - *Juniperus virginiana* |
| Southern Redcedar - *Juniperus siliciola* |
| Junipers |
| Ashe Juniper - *Juniperus ashei* |
| Pinchot Juniper - *Juniperus pinchotii* |
| Common Juniper - *Juniperus communis* |

Select varieties of trees (hardwood and softwood) which have been treated with the RSB have shown increased adventitious rooting. For other trees or plants that can be treated with the RSB, see the Audubon Society, Field Guide of North American Trees, Eastern and Western Regions, Alfred A. Knopf, New York and other guides of other regions of the United States and the World.

From the description of the invention it will be seen that the RSB need not be alive for the treatment of the target plant. The RSB may be in the form of a dried (or partially dried) composition; it may be freeze dried with or without the aqueous medium. The bacterial extract of the aqueous medium may be concentrated to the degree desired to a solid (e.g., powder or granulated) form. Such concentrate is likely to be very useful as a root stimulant.

It is believed that the active principle(s) is likely to be an organic molecule. Accordingly, any method suitable for extracting this molecule(s) can be employed. Once isolated the molecule will be identified and tested for its effect on the plant. At the appropriate time synthesis thereof can be effectuated or conceivably, the gene coding for such molecule(s) can be made to express said molecule.

The following non-limiting examples are presented in order to describe preferred embodiments of this invention.

EXAMPLE 1

Characterization of RSB

The bacteria were grown for 3 days in the medium. Genomic DNA was isolated from the bacteria using the procedure of Rogers, et al. The DNA pellet, thus extracted, was resuspended in 50 microliters of TE buffer (10 mM Tris-HCL, 1 mM EDTA at ph 8.0). This preparation was used as a stock of genomic DNA for all subsequent reactions.

A 10 ng/microliter solution was prepared from the original stock by diluting with TE buffer. A polymerase chain reaction (PCR) was used to selectively amplify the section of DNA that encodes the 16S ribosomal gene. Amplification primers were synthesized on an Applied Biosystems model 381 synthesizer. The following primer sequences were synthesized:

---
5' forward amplification primer: (Seq. I.D. No. 1)
5'- AGA GTT TGA TCM TGG CTC AG -3'
3' reverse amplification primer: (Seq. I.D. No. 2)
5'- GGT TAC CTT GTT ACG ACT T -3'
M = A or C
---

The forward primer corresponds to positions 8–27 of *Escherichia coli* rRNA and the reverse primer corresponds to the complement of positions 1492–1510. The PCR was performed as recommended in the GeneAmp kit (Perkin Elmer Cetus, Norwalk, Conn.) using Amplitaq DNA polymerase (Perkin Elmer Cetus, Norwalk, Conn.) as the amplifying enzyme.

The amplified fragment was used for a preliminary sequence analysis according to Böttger, using the forward and the reverse PCR primers as sequencing primers. The data were compared to sequence data available in the GenBank database.

The PCR amplified fragment was gel-purified and prepared for cloning by treatment with T4 polynucleotide kinase and T4 DNA polymerase. Overhangs at the 3' ends were filled in with T4 DNA polymerase in the presence of all 4 nucleotides to generate blunt ends.

The plasmid pBluescript KS (Stratagene, Stratagone Cloning Systems, La Jolla, Calif.) was digested with the restriction enzyme, SmaI, and terminal phosphates were removed using calf intestinal alkaline phosphatase in order to reduce self-religation. 250 ng of this linearized phosphatase-treated pBS-KS DNA was ligated overnight at 16° C. to 400 ng of RSB 16S rRNA DNA using T7 DNA ligase. NovaBlue competent cells (Novagen, Madison, Wis.) were transformed with 1 microliter of the ligation reaction and the transformed cells selected and amplified.

DNA was extracted from the amplified colonies by the alkaline-lysis method. Two colonies contained plasmids with inserts of the correct size. The presence of the clone with the proper insert was verified by Southern blotting hybridization with a probe made from the purified PCR product and by sequence analysis using the universal M13 −40 primer and the universal M13 reverse primer.

DNA from the two clones was electrophoresed through a 1% TAE-agarose gel and transferred to a nylon membrane according to the standard protocols (Amersham, Amersham International plc., UK). The membrane was incubated in a hybridization solution containing denatured $^{32}$P-labelled probe (made from the purified PCR product). Kodak X-OMAT-AR films were exposed to the blots with two intensifying screens at −70° C. for 19 hours.

Random primer labeling was used to generate radioactive probes (Random Primers DNA Labeling System, GIBCO BRL, Gaithersburg, Md.) using the purified PCR-amplification of the 16S rRNA gene of RSB or pBS-KS vector as a probe template and $\alpha^{32}$P dCTP (3000 Ci/mmole, 10 mCi/ml, ICN Biochemicals Inc., Irvine Calif.) as a radioactive label.

Miniprep DNA was further purified with phenol:chloroform:isoamyl alcohol (25:24:1) and precipitated with ethanol until the A260/A280 ratio was 1.99. The DNA was denatured by the alkali denaturation protocol recommended in the Sequenase Version 2.0 sequencing kit (United States Biochemical, Cleveland Ohio). 35S-dATP (1415 Ci/mmol, 12.5 mCi/ml, NEN, DuPont, Wilmington Del.) was used as the radioactive label.

Sequencing reactions were electrophoresed on a 6% polyacrylamide (19:1 acrylamide: bis-acrylamide), 48% urea gel. Kodak X-Omat AR X-ray films were overlaid on the gels and exposed for 36 hours. Sequencing gels were read manually and proof-read several times until all ambiguities were resolved.

Sequence data were transferred to the VAX cluster mainframe computer (University of Tennessee, Knoxville, Tenn., U.S.A., Computing Center). Data files were converted into "UWGCG" (University of Wisconsin, Madison, Wis., U.S.A., Genetics Computer Group) formats. A comparison of the sequences determined from the two clones and that of the PCR product showed that the clones carried the correct insert. Primers were selected by comparison of sequences with Genbank 16S rRNA sequences from *Caulobacter subvibrioides* (Genbank M83797), *Flavobacterium capsulatum* (Genbank M9296) and *Erythrobacter longus* (Genbank M59062).

A rDNA sequence matrix was created with aligned 16S rDNA sequences obtained from the Ribosomal Database Project (RDP). RSB and other relevant 16S rDNA sequences obtained from Genbank were manually aligned with the RDP sequences using the LINEUP program in the UWGCG package. All spaces were replaced with Xs.

The file containing the aligned sequence matrix was formatted into the PAUP (Phylogenetic Analysis Using Parsimony, Version 3.0) format for further analysis. The matrix consisted of 18 aligned 16S rDNA sequences including RSB. See Table 3.

TABLE 3

| TAXON | DATA BANK ACCESSION NUMBER |
|---|---|
| *Caulobacter subvibrioides* | GenBank M83797 |
| *Caulobacter bacteroides* | GenBank M83796 |
| *Caulobacter crescentus* | GenBank M83798 |
| *Sphingomonas paucimobilis* | GenBank D16144 |
| *Flavobacterium devorans* | ATCC 10829 |
| *Zymomonas mobilis mobilis* | ATCC 10988 |
| *Zymomonas mobilis pomaceae* | ATCC 29192 |
| *Porphyrobacter neustonensis* | GenBank L01785 |
| *Erythrobacter longus* | GenBank M59062 |
| *Sphingomonas capsulata* | ATCC 14666 |
| *Flavobacterium capsulatum* | GenBank M59296 |
| *Rhodospirillum salexigenes* | GenBank M59070 |
| marine *Caulobacter* strain 18 | GenBank M83809 |
| marine *Caulobacter* strain 6 | GenBank M83811 |
| marine *Caulobacter* strain 24 | GenBank M83810 |
| *Pseudomanas diminuta* | GenBank M59064 |
| *Hyphomonas jannaschiana* | Genbank M83806 |
| RSB | |

18 representative members of the relevant branches of the α subdivision of Proteobacter, including RSB, whose 16S rDNA sequences were used in the phylogenetic analysis. These were selected from GenBank and the RDP.

PCR amplification of the genomic DNA preparation produced a single electrophoretically resolvable band of DNA having the expected size of ≈1.5 kbp. The amplification procedure yielded four µg of DNA per 100 µl reaction. There were no artifacts or contaminations detected in the reaction. Direct sequencing of the PCR products was found to be reliable when the amplification primers were used as sequencing primers.

The PCR product was cloned into pBS-KS. The ligation of the insert into the vector was verified by Southern hybridization with probes for the vector made from the linearized vector (pBluescript KS digested with SmaI), while the probe for the insert was made from the gel purified PCR product. Sequencing from the plasmid using the universal M13 –40 primer and the M13 reverse primer verified the identity of the insert.

The complete sequence of the gene is presented in FIG. 7, Seq. I.D. No. 6. The sequence of positions 1–250 and the complement of positions 1250–1446 of RSB 16S rDNA, obtained by directly sequencing the PCR product using the amplification primers as sequencing primers, were entered into the UWGCG package for sequence analysis. The sequence of bases 1–250 and the compliment of 1250–1446 has a high homology (>89%) with the sequence of the 16S rRNA genes of *Caulobacter subvibrioides* (Genbank M83797) Seq. I.D. No. 3, *Flavobacterium capsulatum* (Genbank M59296) Seq. I.D. No. 5 and *Erythrobacter longus* (Gertbank M59062). It also shows a difference of approximately 10%. Internal sequencing primers were designed by comparing the homology within the sequences mentioned above and the sequence of pRSB16SR bases 1–250 and 1250–1446 where applicable. Data obtained by sequencing with the various primers were compiled. Primers were designed to cover sectors which were missed or did not yield satisfactory results.

The evolutionary affiliations of RSB within the subdivision were determined by parsimony analysis using PAUP version 3.0 for Macintosh.

The most parsimonious tree obtained by the exhaustive search places RSB closest to *C. subvibrioides*, see FIG. 8. This relationship is also evident from the distance table. See Table 4. The pair-wise mean distance between RSB and *C. subvibrioides* is 0.040 while the absolute distance is only 45. The absolute distance is the total number of nucleotide difference between 2 taxa considered. The mean distance is the average number of nucleotide differences per nucleotide.

TABLE 4

Pairwise distances between closely related taxa:

| | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 1 *C. bacteroides* | — | 0.048 | 0.130 | 0.139 | 0.108 | 0.107 | 0.132 | 0.134 | 0.140 | 0.142 | 0.139 | 0.134 | 0.143 | 0.139 | 0.049 | 0.118 | 0.048 | 0.143 |
| 2 *C. crescentus* | 54 | — | 0.137 | 0.146 | 0.120 | 0.118 | 0.145 | 0.144 | 0.149 | 0.152 | 0.150 | 0.147 | 0.147 | 0.150 | 0.072 | 0.127 | 0.067 | 0.149 |
| 3 *C. subvibrioides* | 146 | 154 | — | 0.047 | 0.129 | 0.131 | 0.07 | 0.120 | 0.068 | 0.085 | 0.085 | 0.078 | 0.040 | 0.068 | 0.128 | 0.131 | 0.126 | 0.060 |
| 4 *F. devorans* | 156 | 164 | 53 | — | 0.142 | 0.143 | 0.082 | 0.116 | 0.077 | 0.088 | 0.086 | 0.080 | 0.049 | 0.078 | 0.126 | 0.130 | 0.127 | 0.019 |
| 5 MCS18 | 121 | 135 | 145 | 160 | — | 0.002 | 0.137 | 0.131 | 0.140 | 0.134 | 0.138 | 0.137 | 0.143 | 0.139 | 0.121 | 0.081 | 0.111 | 0.154 |
| 6 MCS6 | 120 | 133 | 147 | 161 | 2 | — | 0.138 | 0.130 | 0.142 | 0.134 | 0.139 | 0.139 | 0.144 | 0.141 | 0.121 | 0.081 | 0.111 | 0.155 |
| 7 *P. neustonensis* | 148 | 162 | 83 | 92 | 153 | 154 | — | 0.121 | 0.062 | 0.099 | 0.097 | 0.037 | 0.078 | 0.061 | 0.123 | 0.125 | 0.123 | 0.097 |
| 8 *R. salexigenes* | 150 | 161 | 134 | 130 | 147 | 146 | 135 | — | 0.112 | 0.138 | 0.136 | 0.122 | 0.119 | 0.112 | 0.140 | 0.122 | 0.133 | 0.132 |
| 9 *S. capsulata* | 157 | 167 | 76 | 87 | 157 | 159 | 70 | 126 | — | 0.098 | 0.096 | 0.072 | 0.073 | 0.001 | 0.134 | 0.121 | 0.138 | 0.092 |
| 10 *Z. m.mobilis* | 159 | 171 | 96 | 99 | 150 | 151 | 111 | 155 | 110 | — | 0.011 | 0.092 | 0.092 | 0.096 | 0.139 | 0.138 | 0.142 | 0.098 |
| 11 *Z. m.pomaceae* | 156 | 168 | 95 | 97 | 155 | 156 | 109 | 153 | 108 | 12 | — | 0.090 | 0.089 | 0.094 | 0.134 | 0.136 | 0.136 | 0.095 |
| 12 *E. longus* | 150 | 165 | 88 | 90 | 154 | 156 | 41 | 137 | 81 | 103 | 101 | — | 0.082 | 0.070 | 0.125 | 0.124 | 0.129 | 0.093 |
| 13 RSB | 161 | 165 | 45 | 55 | 161 | 162 | 87 | 133 | 82 | 103 | 100 | 92 | — | 0.071 | 0.135 | 0.137 | 0.137 | 0.061 |
| 14 *F. capsulatum* | 156 | 168 | 76 | 87 | 156 | 158 | 68 | 126 | 1 | 108 | 106 | 79 | 80 | — | 0.132 | 0.119 | 0.136 | 0.092 |
| 15 MCS24 | 55 | 81 | 143 | 141 | 135 | 135 | 137 | 156 | 150 | 155 | 150 | 140 | 151 | 148 | — | 0.121 | 0.026 | 0.131 |
| 16 *H. jannaschiana* | 132 | 142 | 146 | 145 | 90 | 90 | 139 | 136 | 135 | 154 | 152 | 138 | 153 | 133 | 134 | — | 0.114 | 0.137 |
| 17 *P. diminuta* | 54 | 75 | 141 | 143 | 125 | 125 | 138 | 149 | 155 | 159 | 153 | 145 | 154 | 153 | 29 | 127 | — | 0.131 |
| 18 *S. paucimobilis* | 161 | 167 | 67 | 21 | 173 | 174 | 108 | 148 | 108 | 110 | 107 | 104 | 68 | 108 | 147 | 151 | 147 | — |

Below diagonal: Absolute distances
Above diagonal: Mean distances (adjusted for missing data)

EXAMPLE 2

Induction of Adventitious Rooting with RSB

In one preferred embodiment, improved slash pine seedlings (*Pinus elliottii*) (ITT Orchard; International Seed Company) were germinated and grown from 6 to 24 weeks in a laboratory in an autoclave mixture of two parts Peat-Lite™ germination mix to one part medium sized vermiculite. Temperature was maintained at 24°±3° C. and the plants were sprayed weekly with 350 milligrams per liter Captan™. An additional Captan treatment was given the day prior to harvest. White pine seedlings were germinated and grown for twelve weeks under the same culture conditions.

Explants were cultured on basal medium (GD: Gresshoff and Doy medium 1 as modified by Sommer), supplemented with 0.5% activated charcoal and solidified with 1.0% Bacto™ agar. The pH of the medium was adjusted to 5.5 with 0.01N KOH or HCl as needed. Medium was dispensed into 25 by 150 mm culture tubes and 20 ml aliquots before steam autoclaving at 1.27 kg/cm$^2$ (121 C) for 20 minutes.

Seedlings were cut approximately 3 cm below the stem apex in two lots of 50 and immersed directly into 1 L double distilled H$_2$O containing 1 ml Tween-20™. The explants were then transferred through a series of surface sterilization dips as described by Burns and Schwarz. All aqueous solutions were mixed in a laminar flow hood using steam autoclaved water. All ethanol solutions were made with filter sterilized 95% ethanol. Vacuum filtration was accomplished using a sterile 47 mm Millipore™ steel filter funnel fitted with an MSI™ 0.22 μ47 mm nylon filter.

Hypocotylary explants were immersed in 70% ethanol+ 0.1% dimethylsulfoxide (DMSO) for 30 sec while stirring constantly. The plants were drained of the ethanol and immersed in a water solution containing 1.05% sodium hypochlorite (20% commercial bleach) plus Tween-20™ (12 drops/L) for 5 min stirring for 15 sec each minute. Hypocotylary explants were drained and immersed once more in 70% ethanol+0.1% DMSO for 30 sec, stirring continuously. The explants were drained and the above treatment was repeated for 45 sec with continuous agitation. The explants were then placed in a sterile double-distilled H₂O rinse for a maximum of 30 min. They were then allowed to dry in a laminar flow hood on open-faced sterile 14×2 cm petri plates for 10 to 15 min.

The basal end of the hypocotyl was fresh cut and was contacted to a living culture of RSB. The hypocotyl was then inserted 1.0 to 1.5 cm below the surface of the agar. The tubes were then sealed with Parafilm™ as a barrier to airborne contamination before removing them from the laminar flow hood. The explants were maintained in a Sherer™ double-door growth cabinet under fluorescent lights at 27°±2° C. Each treatment group contained 20 individual internal replicates. Data were taken 12 weeks after bacterial exposure.

Six-week-old slash pine seedlings as the source of the hypcotylary explants were used. Over 93% of the cultures containing living RSB produced at least one root, whereas none of the control explants produced roots over the 90 day experiment. See Table 5.

TABLE 5

Percent rooting on bacteria treated seedling explants of slash pine after 90 days in culture.

| TREATMENT | n[a] | PERCENT ROOTED |
|---|---|---|
| Live Bacteria | 30 | 93.3 |
| Culture Filtrate | 32 | 40.6[b] |
| Control | 19 | 00.0 |

[a]Number of explants treated, explants were 6 weeks old at harvest.
[b]100% of these cultures were contaminated with an organism that passed through 0.22 µm filtration.

The roots produced with RSB treatment were similar to normal seedling roots and were indistinguishable from roots produced spontaneously in control cultures. Rooted hypocotylary explants were transferred to soil and were placed under normal greenhouse conditions designed for in vitro plantlet transitioning. Plantlet survival after 15 weeks in the greenhouse exceeded 95%. The plants were then transferred to the outdoors, to a field where they grew normally. See FIG. 12.

EXAMPLE 3

Root Morphology Following RSB Treatment

The morphology of RSB-stimulated roots in slash pine is shown in FIG. 11 after 6 weeks of in vitro culture. Both single and branched primary roots are produced. Some of the microplants are beginning to develop secondary branching which is the precursor of a well-developed secondary fibrous root system. Such secondary fibrous root system is observed when the pine tree is grown outdoors.

EXAMPLE 4

White Pine

RSB was also tested on 12-week-old hypocotylary explants of white pine (*Pinus strobus*). RSB treated plants displayed significant levels of rooting were observed after 7 weeks in culture (42%) compared to controls which showed no rooting (See FIG. 9). FIG. 10 illustrates the typical in vitro growth pattern accompanying a positive rooting response found in RSB co-cultures of both slash and white pine explants. In FIG. 10, the RSB treated explant on the right shows increased rooting compared to the non-treated control explant on the left.

EXAMPLE 5

Effect of Seed Source on RSB Root Stimulation

The effect of seed source on adventitious rooting stimulated by RSB was also determined. Two seed sources were tested using explants obtained from seedlings grown for 12 weeks before harvesting. See Table 6. The experimental methodology was as described for the other rooting trials, except that seedling explants of equal age were obtained from two separate seed sources. Each treatment consisted of 20 explants, for a total of 80 individuals. In each case, exposure to RSB produced a substantial increase in adventitious rooting over control levels. Adventitious rooting improvement with RSB was obtained with open-pollinated seed sources and using seed derived from full-sib crosses.

TABLE 6

Bacterial stimulation of adventitious rooting of hypocotylary explants of 3-month-old slash pine seedlings obtained from two seed sources. (Seed source: Improved slash pine, ITT Orchard and Bay Co. FL/International Seed Co.; Data taken 12 weeks after culture initiation)

| | PERCENT ROOTED SEEDLING SOURCE | |
|---|---|---|
| TREATMENT | ITT ORCHARD | BAY CO., FL |
| RSB | 75 | 60 |
| control | 25 | 16 |

EXAMPLE 6

Long Term Growth Without Pathology Following Treatment with RSB

Hypocotylary explants of White pine were dipped into live colonies of RSB as described previously. Following treatment with RSB, the explants were placed in a standard greenhouse into Conetainer™. After several months of growth in the greenhouse, the White pine plants were transplanted to an outdoor garden. In the garden, the plants have developed normally and continue to grow normally.

EXAMPLE 7

Induction of Adventitious Rooting with RSB in Other Conifers

Seedlings of Loblolly Pine (*Pinus taeda*), White Spruce, (*Picea glauca*), and European Latch (*Larix laricina*) are cut approximately three centimeters below the stem apex and immersed into a mixture of distilled H₂O and Tween-20™ as described above for slash pine seedlings. The explants are then prepared for treatment with RSB as described above for slash pine explants.

The basal end of the hypocotyl is fresh cut and is contacted to a living culture of RSB as described above for slash pine and white pine. The hypocotyl explants are then placed in a standard greenhouse into Conetainers™.

About 90 days following treatment, a high percentage of the hypocotyls have formed roots, as compared with control untreated hypocotyl explants. The root structure of the treated Loblolly pines, White Spruce, and European Larch is indistinguishable from that of untreated wild rooted plants of the same species. Both single and primary roots are produced, with some of the cuttings beginning to develop secondary root branching.

Greater than 90% of the plants survive five months post-treatment with RSB. At that time, plants are transferred outdoors to a field where they continue to grow normally.

Hedgings (cuttings) taken from established stools of loblolly pine were dipped into living cultures of RSB. The hedgings were then stuck into a peat:perlite (50:50) mixture and placed under mist in the greenhouse. Hedgings were incubated for 12 weeks before rooting data was taken. One of the genotypes tested responded by 20% rooting over the non-treated controls.

EXAMPLE 8

Induction of Adventitious Rooting of Non-Coniferous Species with RSB

Because conifers are a particularly difficult type of plant in which to promote rooting, it was hoped that the same effect could be observed in non-coniferous plants, including hardwood and softwood trees and fruit and vegetable producing monocotyledonous and dicotyledonous plants. It has been discovered that indeed the root inducing effect of RSB does occur with explants of trees other than conifers.

Trees of the genus Casuarina are a distinctive family of trees and shrubs adapted to dry habitats in regions of high temperature and low rainfall and are distributed widely in northeast Australia, Malaysia, New Caledonia, Fiji, and the Mascarene Islands. The wood from several species of Casuarina is extremely hard and is valued for furniture manufacture. Red beefwood, *Casuarina equisetifolia*, is the most widely cultivated species. Other valuable timbers include the Australian native *C. stricta*, the she oak, and the cultivated species *C. cunninghamiana*, the river oak.

The basal end of a 2 to 3 cm microcutting of *C. cunninghamiana*, obtained from in vitro propagated stock cultures, was contacted to a living culture of RSB. The microcutting basal end was then inserted in a test tube 1.0 to 1.5 cm below the surface in agar containing the full strength medium formulation of Gresshoff and Doy. No charcoal was added to the medium. The tubes were then sealed with Parafilm™ as a barrier to airborne contamination before removing them from the laminar flow hood. The explants were maintained in a controlled environment growth chamber under an 18 hour light and 6 hour dark photoperiod at 27°±2° C. for 23 days, at which time the roots were examined. See Table 7.

TABLE 7

EFFECT OF RSB ON ADVENTITIOUS ROOT FORMATION ON MICROCUTTINGS OF IN VITRO PROPAGATED *CASUARINA CUNNINGHAMIANA*

| TREATMENT | NUMBER TREATED | PERCENT ROOTED[1] | PRIMARY ROOTS[2] |
|---|---|---|---|
| RSB | 31 | 87.1[a] | 8.4 ± 5.5[a] |
| CONTROL | 34 | 41.2[b] | 1.5 ± 2.4[b] |

[1]Rooting percentages with different superscripts are significantly different at 5% level of error. (Fishers LSD Method)
[2]Primary rooting data are presented as averages ± S.D., averages with different superscripts are significantly different at 5% level of error. (Fishers LSD Method)

RSB exposure caused slightly more than a doubling of adventitious root induction over the spontaneous background rooting found in the control population, from 41 to 87%. In addition, the number of primary roots in the RSB treated explants was found to be slightly more than five times the number present in the controls.

The surprising results in Casuarina, especially concerning the stimulation of increased number of primary roots as compared to controls, demonstrates the potential importance of RSB in non-conifer woody species used in re-forestration of agriculturally marginal lands throughout the subtropical and tropical world. Not only did the treated Casuarina develop adventitious roots more readily than the controls, but the treated plants developed more roots than did the controls. The increased root/shoot ratio produced in the presence of RSB may provide an advantage with respect to increased stress tolerance and early survivability of these plants upon outplanting to the field.

Other deciduous trees, including magnolia and maple were also treated by contacting to live cultures of RSB. Rooting in the treated plants was found to be greater than in controls. Following treatment, the plants grew well under normal conditions.

Unexpectedly, RSB was shown to stimulate rooting in deciduous trees as well as in conifers. It is anticipated that RSB will induce root formation in the following non-limiting examples of magnolia and maple trees (see Table 8).

TABLE 8

| Maple Family (Aceraceae) |
|---|
| Florida Maple - *Acer barbatum* |
| Chalk Maple - *Acer lencoderine* |
| Boxelder - *Acer negundo* |
| Black Maple - *Acer nigrum* |
| Striped Maple - *Acer pensylvanicum* |
| Norway Maple - *Acer platanoides* |
| Planetree Maple - *Acer pseudoplatanus* |
| Red Maple - *Acer rubrum* |
| Silver Maple - *Acer saccharinum* |
| Sugar Maple - *Acer saccarum* |
| Mountain Maple - *Acer spicatum* |
| Magnolia Family (Magnoliaceae) |
| Florida Anise-tree - *Illicium floridanum* |
| Yellow Anise-tree - *Illicium parviflorum* |
| Yellow-poplar - *Liriodendron tulipifera* |
| Cucumbertree - *Magnolia acuminata* |
| Ashe Magnolia - *Magnolia ashei* |
| Fraser Magnolia - *Magnolia fraseri* |
| Southern Magnolia - *Magnolia grandiflora* |
| Bigleaf Magnolia - *Magnolia macrophylla* |
| Pyramid Magnolia - *Magnolia pyramidata* |
| Saucer Magnolia - *Magnolia soulangiana* |
| Umbrella Magnolia - *Magnolia tripetala* |
| Sweetbay - *Magnolia virginiana* |

In contrast to the stimulation of adventitious rooting in plants as the result of co-culturing with bacteria other than RSB, the plants co-cultured with RSB or treated with the bacteria free RSB extract produced a functional root system without any apparent pathology to the plant caused by the inducing organism. Adventitious root production by RSB is seen to be accomplished by a nontransformation mechanism. Thus, it is within the scope of the invention that cuttings from a plant whose roots have been promoted by the RSB (or by extracts) will have a greater facility to root than if the cutting had been from a plant that had not been exposed to the RSB. Thus, the plant parts of RSB stimulated plants are within the scope of the invention.

While the scope of the present invention is not to be limited by any one particular theory, the rooting inducing properties of RSB could De due to the synthesis by RSB of a chemical molecule which induces rooting. The nature of this theorized molecule is unknown and may represent a heretofore undiscovered growth or rooting factor. The production by RSB of a factor which induces rooting is evidenced by the fact that RSB free extracts, in which RSB had previously grown, are capable of inducing rooting, as is described in the following examples. It is well understood that in accordance with the invention the RSB extract contains one or more molecules which assist or promote the rooting of plants as herein described. Accordingly, it is proposed to analyze the extract for the one or more active molecules, screen the molecules for activity similar or identical to that of the RSB and if necessary to identify the one or more active molecules. As occurs, not infrequently with serendipitous inventions, as here, a reserch program will proceed henceforth to more fully identify the active molecule.

EXAMPLE 9

Production of Bacteria Free Extract Capable of Inducing Rooting

Two liters of "enhanced" WPM (pH-5.2) were inoculated with 200 µL medium and shaken at 130 rpm for 5 days at 27° C. in the dark. The medium was then stored at 4° C. until extracted. The medium was centrifuged twice at 10000 rpm for 30 min, until the supernatant was clear and free of suspended particulates. The medium was transferred into a 2 liter flask and filtered through a sterile 0.2 µm nylon filter. The medium was then divided into four portions of 500 ml each and extracted with 4 portions of 250 ml of ethyl acetate. The final ethyl acetate extract was pooled, washed once with distilled water and dried with an excess of anhydrous sodium sulfate. The extracted medium was acidulated to a pH of 2.8 with 1N HCl. The above extraction procedure was repeated with a fresh batch of ethyl acetate. The two ethyl acetate extracts were then distilled under vacuum using a Rotavapor R, Brinkmann Instruments, Westbury, N.Y. After all the solvent was evaporated, the residue was dissolved in 2 ml of 100% ethanol and diluted with distilled water to a volume of 85 ml. The extracts (pH 5.2 and pH 2.8) were stored under refrigeration at 37° C. The extract for best results should be modified within a pH optimum to contain the presumed active molecule, such as about 3.0 to about 2.0 depending on the nature of the molecule. Other appropriate extension conditions can be developed by one skilled in the art.

EXAMPLE 10

Method of Use of Bacteria Free Extract to Promote Rooting

RSB culture extract as described above was added to half-strength Gresshoff and Doy medium (GD) (50 mL to 950 mL respectively). The RSB extract was passed through a 0.2 µm filter and added to partially cooled (50° C.) autoclaved medium and thoroughly mixed before dispensing into culture tubes. Slash pine seedling explants (prepared as previously described) were inserted into the solidified GD medium and incubated for 9 weeks as previously described. Rooting data is presented in Table 9.

TABLE 9

Effect of various RSB culture extracts on adventitious rooting of slash pine (*Pinus elliottii*) seedling hypocotylary explants after a 9 week culture period.

| TREATMENT[1] | NUMBER TREATED | ROOTING % OF EXPLANTS[2] |
|---|---|---|
| RSB | 20 | 45[a] |
| pH 2.8 | 20 | 30[ab] |
| pH 5.2 | 20 | 20[cb] |
| MIXTURE (2.8 + 5.2) | 18 | 11[cb] |
| CONTROL | 20 | 0[c] |

[1]Hypocotylary explants were obtained from 5 month old seedlings. RSB culture medium was pasted through a 0.2 µ sterile filter and extracted with ethyl acetate at pH 2.8 and 5.2. Extracts were reduced to dryness and taken up in a absolute ethanol and brought to a standard volume with distilled water. Extracts were added back to solidified half-strength Gresshoff and Doy medium plus 0.5% charcoal.
[2]Rooting percentages with different superscripts are significantly different at the 5% level of error. (Fishers LSD Method)

Growth medium treated with RSB and extract of growth medium in which plants previously treated with RSB have grown can induce spontaneous rooting of shoots. In this manner extract of growth medium which contained RSB can be stored for future use in any form desired, liquid (concentrated or not), dehydrated solid (powder or granulate) or freeze dried.

The RSB and the RSB free extract of the present invention represent a significant step forward in the promotion of rooting in plants, particularly in the conifer species. The treated trees grow without pathology, forming roots at a much increased rate than untreated control trees. The use of RSB to stimulate rooting appears to have wide applicability to all kinds of plants, both monocotyledons and dicotyledons.

It will be understood that many variations can be made in the procedures described for the use of RSB to promote rooting while still remaining within the bounds of the present invention. It is the intention of the inventors that such variations should be included within the scope of their invention if found defined within the following claims.

BIBLIOGRAPHY (1) Barlow, P. W., "The Origin, Diversity and Biology of Shoot-Borne Roots," *Biology of Adventitious Root Formation*, Basic Life Sciences, Vol. 62, 1994.

(2) Blakesley, D., "Auxin Metabolism and Adventitious Root Initiation," *Biology of Adventitious Root Formation*, Basic Life Sciences, Vol. 62, Plenum Press, 1994.

(3) Böttger, E. C. 1989. Rapid determination of bacterial ribosomal RNA sequences by direct sequencing of enzymatically amplified DNA. Federation of European Microbiological Societies-Microbiology Letters 65 (1989) 171–176.

(4) Burns, J. A., O. J. Schwarz, and S. E. Schlarbaum. 1991. Multiple shoot production from seedling explants of slash pine (*Pinus elliottii*, Englem.). Plant Cell Reports. 10: 439–443.

(5) Devereux, J., P. Haeberli, and O. Smithies. 1984. A Comprehensive Set of Sequence Analysis Programs for the VAX. Nucleic Acid Research. 12(1): 387–395.

(6) Eden, P. A., T. M. Schmidt, R. P. Blakemore, and N. R. Pace. 1991. Phylogenetic analysis of *Aquaspirillum magnetotacticum* using polymerase chain reaction-amplified 16S rRNA-specific DNA. int. J. of Syst. Bact. April 1991, 324–325.

(7) Gay, G., "Effect on the ectomycorrhizal fungus *Hebeloma hiemale* on adventitious root formation in derooted *Pinus halepensis* shoot hypocotyls", Canadian Journal of Botany, 1989.

(8) Hassig, B. E. and T. D. Davis, "A Historical Evaluation of Adventitious Rooting Research to 1993," *Biology of Adventitious Root Formation*, Basic Life Sciences, Vol. 62, Plenum Press, 1994.

(9) Howard, B. H., "Manipulating Rooting Potential in Stockplants Before Collecting Cuttings," *Biology of Adventitious Root Formation*, Basic Life Sciences, Vol. 62, Plenum Press, 1994.

(10) Lloyd, G. and B. H. McCown. 1980. Commercially-feasible micropropagation of mountain laurel, *Kalmia Latifolia*, by use of shoot-tip culture. Somb. Proc. International Plant Prop. Soc. 30:421–427

(11) Maniatis, T., J. Sambrook, and E. F. Fritsch. 1989. Molecular Cloning. A Laboratory Manual, 2nd Ed. Cold Spring Harbour Laboratory Press, Cold Spring Harbour, N.Y.

(12) Mullis, K. B. and F. A. Faloona. 1987. Specific Synthesis of DNA in vitro via a polymerase-catalyzed chain reaction. Meth. Enzym. 155: 335–350.

(13) Olsen, G. J., N. Larsen, and C. R. Woese. 1991. Nucleic Acid Research. 19, 2017–2021.

(14) Ritchie, G. A., "Commercial Application of Adventitious Rooting to Forestry", *Biology of Adventitious Root formation*, in Basic Life Sciences, Vol. 62, Plenum Press, 1994.

(15) Rogers, S. O., S. Rehner, C. Bledsoe, G. J. Mueller, and F. Ammirati. 1989. Extraction of DNA from Basiodiomycetes for ribosomal DNA hybridizations. Can. J. Bot. 67: 1235–1243.

(16) Saiki, R. K., S. J. Scharf, F. Faloona, K. B. Mullis, G. T. Horn, H. A. Erlich, and N. Arnheim. 1985. Enzymatic amplification of β-globin genomic sequences and restriction site analysis of sickle cell anemia. Science. 230: 1350–1354.

(17) Sommer, H. E., C. L. Brown, and P. P. Kormanik. 1975. Differentiation of plantlets in longleaf pine (*Pinus palustris* Mill) tissue cultured in vitro. Botanical Gazette. 136(2): 196–200.

(18) Stein & Fortin, "Pattern of root initiation by an ectomycorrhizal fungus on hypocotyl cuttings of *Larix laricina*", Canadian Journal of Botany, 1990.

(19) Swofford, D. L. 1991. PAUP: Phylogenetic Analysis Using Parsimony, Version 3.1. Computer program distributed by the Illinois Natural History Survey, Champaign, Ill.

What is claimed is:

1. An isolated bacteria which has its 16S rRNA transcribed from a nucleotide sequence which comprises the DNA sequence shown in Sequence ID No. 6, and which is capable of inducing adventitious root formation in plants without pathogenicity to the plants.

2. The isolated bacteria of claim 1 wherein the plants are conifers.

3. The isolated bacteria of claim 2 wherein the conifers are of the genus Pinus.

4. The isolated bacteria of claim 3 wherein the pine are selected from the group consisting of white pine (*Pinus strobus*) and slash pine (*Pinus elliottii*).

5. The isolated bacteria of claim 1 wherein the plants are deciduous trees selected from the group consisting of magnolia, maple, and *Casuarina spp*.

6. The isolated bacteria of claim 1 which has the following morphological characteristics: gram negative, rod-shaped, vibrioid or fusiform cells, about 0.65 to 0.7 μm in length, stalked, said stalk terminated by a holdfast, and motile cells having a singular polar flagellum.

7. A method for inducing adventitious root formation in a plant selected from the group consisting of evergreens and deciduous trees, without pathogenicity to the plant which comprises contacting a part of the plant, other than a root, to a bacteria which is capable of inducing adventitious root formation in the plant without pathogenicity to the plant, which bacteria has its 16S rRNA transcribed from the DNA sequence shown in Sequence ID No. 6, or to a growth medium in which the bacteria was grown, and planting the plant in a suitable growth medium for the plant.

8. The method of claim 7 which further comprises growing the plant until adventitious roots are formed.

9. The method of claim 7 which further comprises growing the plant in ambient conditions.

10. The method of claim 7 wherein the plants are conifers.

11. The method of claim 10 wherein the conifers are of the genus Pinus.

12. The method of claim 11 wherein the pine are selected from the group consisting of white pine (*Pinus strobus*) and slash pine (*Pinus elliottii*).

13. The method of claim 7 wherein the deciduous trees are selected from the group consisting of maple, magnolia, and *Casuarina spp*.

14. A living cutting of a plant in which adventitious roots have been induced by exposure to the bacteria of claim 1, or by exposure to a growth medium in which the isolated bacteria had previously grown.

15. The living cutting of claim 14 which is a cutting of a conifer.

16. The living cutting of claim 15 wherein the conifer is of the genus Pinus.

17. The living cutting of claim 16 wherein the conifer is selected from the group consisting of white pine (*Pinus strobus*) and slash pine (*Pinus elliottii*).

18. The living cutting of claim 14 which is a cutting of a deciduous tree.

19. The living cutting of claim 18 wherein the deciduous tree is selected from the group consisting of magnolia, maple, and *Casuarina spp*.

20. A root stimulating growth medium in which the isolated root stimulating bacteria of claim 1 had previously grown.

21. The isolated bacteria of claim 1 which is a member of the α subdivision of Proteobacteria.

22. The method of claim 7 wherein the bacteria is a member of the α subdivision of Proteobacteria.

23. The method of claim 7 wherein the bacteria is live.

24. A method for inducing adventitious root formation in a plant, without pathogenicity to the plant which comprises contacting a part of the plant other than a root to a bacteria which is capable of inducing adventitious root formation in the plant without pathogenicity to the plant, which bacteria has its 16S rRNA transcribed from the DNA sequence shown in Sequence ID No. 6, or to a growth medium in which the bacteria was grown, and planting the plant in a suitable growth medium for the plant.

25. The method of claim 24 wherein the bacteria is a member of the α subdivision of Proteobacteria.

26. The method of claim 25 wherein the induction of adventitious root formation is caused by a bacteria which causes a mustard-yellow contaminant on slash pine cultures grown in vitro.

27. The isolated bacteria of claim 1 which has accession No. ATCC 55580.

28. The method of claim 7 wherein the bacteria has accession No. ATCC 55580.

29. The root stimulating bacterial growth medium of claim 20 which is free of the bacteria.

30. The root stimulating bacterial growth medium of claim 20 which is selected from the group consisting of a liquid, a powder solid, a granulate solid, and a freeze dried solid.

31. The root stimulating bacterial growth medium of claim 30 wherein the bacteria has accession No ATCC 55580.

32. A root stimulating bacteria which is obtained by a method which comprises:

growing a pine seedling explant in in vitro agar culture, identifying a contaminant colony around the base of a rooted explant on the agar surface, and isolating a bacteria colony from the contaminant, wherein the bacteria has its 16S rRNA transcribed from the DNA sequence shown in Sequence ID No. 6.

33. The method of claim 22 wherein the induction of adventitious root formation is caused by a species which causes a mustard-yellow contaminant on slash pine cultures grown in vitro.

34. The living cutting of claim 14, which is six to seven weeks old.

* * * * *

UNITED STATES PATENT AND TRADEMARK OFFICE
CERTIFICATE OF CORRECTION

PATENT NO. : 5,629,468

DATED : May 13, 1997

INVENTOR(S) : Schwarz et al

It is certified that error appears in the above-identified patent and that said Letters Patent is hereby corrected as shown below:

Add the attached sequence listing to column 22 after the last claim

Signed and Sealed this

Tenth Day of February, 1998

Attest:

BRUCE LEHMAN

*Attesting Officer*   *Commissioner of Patents and Trademarks*

SEQUENCE LISTING (1) GENERAL INFORMATION (i) APPLICANT: Schwarz, Otto J.
                    Burns, John A.
                    Mullin, Beth C.

(ii) TITLE OF INVENTION: ROOT STIMULATING BACTERIA (iii) NUMBER OF SEQUENCES: 6

(iv) CORRESPONDENCE ADDRESS:
        (A) ADDRESSEE: Weiser & Associates
        (B) STREET: 230 South Fifteenth Street, Suite 500
        (C) CITY: Philadelphia
        (D) STATE: Pennsylvania
        (E) COUNTRY: U.S.A.
        (F) ZIP: 19102

(v) COMPUTER READABLE FORM:
        (A) MEDIUM TYPE: Floppy disk
        (B) COMPUTER: IBM PC compatible
        (C) OPERATING SYSTEM: PC-DOS/MS-DOS
        (D) SOFTWARE: PatentIn Release #1.0, Version #1.25

(vi) CURRENT APPLICATION DATA:
        (A) APPLICATION NUMBER: US 08/354,656
        (B) FILING DATE: 13-DECEMBER-1994
        (C) CLASSIFICATION:

(viii) ATTORNEY/AGENT INFORMATION:
        (A) NAME: Weiser, Gerard J.
        (B) REGISTRATION NUMBER: 19,763
        (C) REFERENCE/DOCKET NUMBER: 372.6129P (ix) TELECOMMUNICATION INFORMATION:
        (A) TELEPHONE: 215-875-8383
        (B) TELEFAX: 215-875-8394
        (C) TELEX: 834809 WEISTAK (2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:1:

AGAGTTTGAT CMTGGCTCAG                                                            20

(2) INFORMATION FOR SEQ ID NO:2:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:2:

GGTTACCTTG TTACGACTT                                                             19

(2) INFORMATION FOR SEQ ID NO:3:

(i) SEQUENCE CHARACTERISTICS:
        (A) LENGTH: 1425 base pairs
        (B) TYPE: nucleic acid
        (C) STRANDEDNESS: double
        (D) TOPOLOGY: linear (vi) ORIGINAL SOURCE:
        (A) ORGANISM: Caulobacter subvibrioides (xi) SEQUENCE DESCRIPTION: SEQ ID NO:3:

AACTTGAGAG TTTNATCCTG GCTCAGAACG AACGCTNGCG GCATGCCTAA CACATGCAAG      60

TCGAACGAGA CCTTCGGGTC TAGTGGCGCA CGGGTGCGTR ACGCGTGGGA ATCTGCCCTT     120

GGGTTCGGAA TAACTCGCCG AAAGGCGTGC TAATACCGGA TGATGTCGTA AGACCAAAGA     180

TTTATCGCCC AGGGATGAGC CCGCGTAAGA TTAGCTAGTT GGTGAGGTAA AGGCTCACCA     240

AGGCGACGAT CTTTAGCTGG TCTGAGAGGA TGATCAGCCA CACTGGGACT GAGACACGGC     300

CCAGACTCCT ACGGGAGGCA GCAGTGGGGA ATATTGGACA ATGGGCGAAA GCCTGATCCA     360

GCAATGCCGC GTGAGTGATG AAGGCCTTAG GGTTGTAAAG CTCTTTTACC CGGGATGATA     420

ATGACAGTAC CGGGAGAATA AGCTCCGGCT AACTCCGTGC CAGCAGCCGC GGTAATACGG     480

AGGGAGCTAG CGTTGTTCGG AATTACTGGG CGTAAAGCGC ACGTAGGCGG CTTTGTAAGT     540

CAGAGGTGAA AGCCTGGAGC TCAACTCCAG AACTGCCTTT GAGACTGCAT CGCTTGAATC     600

CAGGAGAGGT GAGTGGAATT CCGAGTGTAG AGGTGAAATT CGTAGATATT CGGAAGAACA     660

CCAGTGGCGA AGGCGGCTCA CTGGACTGGT ATTGACGCTG AGGTGCGAAA GCGTGGGGAG     720

```
CAAACAGGAT TAGATACCCT GGTAGTCCAC GCCGTAAACG ATGATAACTA GCTGTCCGGG      780

CACTTGGTGC TTGGGTGGCG CAGCTAACGC ATTAAGTTAT CCGCCTGGGG AGTACGGTCG      840

CAAGATTAAA ACTCAAAGGA ATTGACGGGG GCCTGCACAA GCGGTGGAGC ATGTGGTTTA      900

ATTCGAAGNA ACGCGCAGAA CCTTACCAGC GTTTGACATG TCCGGACGAT TTCCAGAGAT      960

GGATCTCTTC CCTTCGGGGA CTGGAACACA GGTGCTGCAT GGCTGTCGTN AGCTCGTGTC     1020

GTGAGATGTT GGGTTAAGTC CCGCAACGAG CGCAACCCTC GCCNNTAGTT ACCATCATTT     1080

AGTTGGGGAC TCTAAAGGAA CCGCCGGTGA TAAGCCGGAG GAAGGTGGGG ATGACGTCAA     1140

GTCCTCATGG CCCTTACGCG CTGGGCTACA CACGTGCTAC AATGGCGGTG ACAGTGGGCA     1200

GCAAACTCGC GAGAGTGCGC TAATCTCCAA AAGCCGTCTC AGTTCGGATT GTTCTCTGCA     1260

ACTCGAGAGC ATGAAGGCGG AATCGCTAGT AATCGCGGAT CAGCATGCCG CGGTGAATAC     1320

GTTCCCAGGC NTTGTACACA CCGCCCGTCA CACCATGGGA GTTGGGTTCA CCCGAAGGCG     1380

TTGCGCTAAC TCGCAAGAGA GGCAGGCGAC CACGGTGGGC TTAGC                    1425
```

(2) INFORMATION FOR SEQ ID NO:4:

(i) SEQUENCE CHARACTERISTICS:
        (A) LENGTH: 1446 base pairs
        (B) TYPE: nucleic acid
        (C) STRANDEDNESS: double
        (D) TOPOLOGY: linear (vi) ORIGINAL SOURCE:
        (A) ORGANISM: Sphingomonas paucimobilis (xi) SEQUENCE DESCRIPTION: SEQ ID NO:4:

```
GAACGAACGC TGGCGGCATG CCTAACACAT GCAAGTCGAA CGAAGGCTTC GGCCTTAGTG       60

GCGCACGGGT GCGTAACGCG TGGGAATCTG CCCTTAGGTT CGGAATAACA GCTGGAAACG      120

GCTGCTAATA CCGGATGATA TCGCGAGATC AAAGATTTAT CGCCTGAGGA TGAGCCCGCG      180

TTGGATTAGG TAGTTGGTGG GGTAAAGGCC TACCAAGCCG ACGATCCATA GCTGGTCTGA      240

GAGGATGATC AGCCACACTG GGACTGAGAC ACGGCCCAGA CTCCTACGGG AGGCAGCAGT      300

GGGGAATATT GGACAATGGG CGAAAGCCTG ATCCAGCAAT GCCGCGTGAG TGATGAAGGC      360

CTAGGGTTG TAAAGCTCTT TTACCCGGGA AGATAATGAC TGTACCGGGA GAATAAGCCC      420

CGGCTAACTC CGTGCCAGCA GCCGCGGTAA TACGGAGGGG GCTAGCGTTG TTCGGAATTA      480
```

```
CTGGGCGTAA AGCGCACGTA GGCGGCTTTG TAAGTCAGAG GTGAAAGCCT GGAGCTCAAC      540

TCCAGAACTG CCTTTGAGAC TGCATCGCTT GAATCCAGGA GAGGTCAGTG GAATTCCGAG      600

TGTAGAGGTG AAATTCGTAG ATATTCGGAA GAACACCAGT GGCGAAGGCG GCTGACTGGA      660

CTGGTATTGA CGCTGAGGTG CGAAAGCGTG GGGAGCAAAC AGGATTAGAT ACCCTGGTAG      720

TCCACGCCGT AAACGATGAT AACTAGCTGT CCGGGCACTT GGTGCTTGGG TGGCGCACGT      780

AACGCATTAA GTTATCCGCC TGGGGAGTAC GGCCGCAAGG TTAAAACTCA AAGGAATTGA      840

CGGGGGCCTG CACAAGCGGT GGAGCATGTG GTTTAATTCG AAGCAACGCG CAGAACCTTA      900

CCAGCGTTTG ACATGGTAGG ACGACTTCCA GAGATGGATT TCTTCTTCGG GGACCTACAC      960

ACAGGTGCTG CATGGCTGTC GTCAGCTCGT GTCGTGAGAT GTTGGGTTAA GTCCCGCAAC     1020

GAGCGCAACC CTCGCCTTTA GTTACCATCA TTTGGTTGGG TACTCTAAAG GANACCGCCG     1080

GTGATAAGCC GGAGGAAGGT GGGGATGACG CCAAGTCCTC ATGGCCCTTA CGCGCTGGGC     1140

TACACACGTG CTACAATGGC AACTACAGTG GGCAGCGACC CTGCGAGGGC GAGCTAATCC     1200

CCAAAAGTTG TCTCAGTTCG GATTGTTCTC TGCAACTCGA GAGCATGAAG GCGGAATCGC     1260

TAGTAATCGC GGATCAGCAT GCCGCGGTGA ATACGTTCCC AGGCCTTGTA CACACCGCCC     1320

GTCACACCAT GGGAGTTGGA TTCACCCGAA GGCGTTGCGC CAACCTAGCA ATAGGAAGCA     1380

GGCGACCACG GTGGGTTCAG CGACTGGGGT GAAGTCGTAA CAAGGTAGCC GTAGGGGAAC     1440
CTGCGG                                                                1446
```

(2) INFORMATION FOR SEQ ID NO:5:

(i) SEQUENCE CHARACTERISTICS:
        (A) LENGTH: 1437 base pairs
        (B) TYPE: nucleic acid
        (C) STRANDEDNESS: double
        (D) TOPOLOGY: linear (vi) ORIGINAL SOURCE:
        (A) ORGANISM: Flavobacterium devorans (xi) SEQUENCE DESCRIPTION: SEQ ID NO:5:

```
NAAACTTGAG AGTTTGATCC TGGCTCAGAA CGAACGCTAG CGGCATGCCT AACACATGCA       60

AGTCGAACGA AGGCTTCGGC CNNAGTGGCG CACGGGTGCG TAACGCGTGG GAATCTGCCC      120

TTAGGTTCGG AATAACAGCT GGAAACGGCT GCTAATACCG GATGATATCG CGAGATCAAA      180
```

```
GATTTATCGC CTGAGGATGA GCCCGCGTTG GATTAGGTAG TTGGTGGGGT AAAGGCCTAC      240
CAAGCCGACG ATCCATAGCT AGTCTGAGAG GATGATCAGC CACACTGGGA CTGAGACACG      300
GCCNAGACTN CNACGGGAGG CAGCAGTGGG GAATATTGGA CAATGGGCGA AAGCCTGATC      360
CAGCAATGCC GCGTGAGTGA TGAAGGCCNT AGGGTTGTAA AGCTNTTTTA CCCGGGAAGA      420
TAATGACTGT ACCGGGAGAA TAAGCCCCGG CTAACTCCGT GCCAGCAGCC NCGGTAATAC      480
GGAGGGGGCN AGCGTTGTTC GGAATTACTG GGCGTAAAGC GCACGTAGGC GGCNTTGTAA      540
GTCAGAGGTG AAAGCCTGGA GCTCAACTCC AGAACTGCCT TTGAGACTGC ATCGCTTGAA      600
TCCAGGAGAG GTCAGTGGAA TTCCGAGTGT AGAGGTGAAA TTCGTAGATA TTCGGAAGAA      660
CACCAGTGGC GAAGGCGGCN GACTGGACTG GNATTGACGC TGAGGTGCNN AAGCGTGGGG      720
AGCAAACAGG ATTAGATACC CTGGTAGTCC ACGCCGTAAA CGATGATAAC TAGCTGTCCG      780
GNCACTTGGT GCTTGGGTGG CGCAGCTAAC GCATTAAGTT ATCCGCCTGG GGAGTACGGC      840
CGCAAGGTTA AAACTCAAAG GAATTGACGG GGGCCTGCAC AAGCGGTGGA GCATGTGGTT      900
TAATTCGAAN NAACGCGCAG AACCTTACCA GCGTTTGACA TGGTAGGACG ACTTCCAGAG      960
ATGGATTTCT TCCCTTCGGG GACCTACACA CAGGTGCTGC ATGGCTGTCG TCAGCTCGTG     1020
TCGTGAGATG TTGGGTTAAG TCCCGCAACG AGCGCAACCC TCGCCNTTAG TTACCATCAT     1080
TTGGTTGGGT ACTCTAAAGG AACCGCCGGT GATAAGCNGG AGGAAGGTGG GGATGACGTC     1140
AAGTCCTCAT GGCCCTTACG CGCTGGGCTA CACACGTGCT ACAATGGCAA CTACAGTGGG     1200
CAGCGACCCT GCGAGGGCGA GCTAATCCCC AAAAGTTGTC TCAGTTCGGA TTGTTCTCTG     1260
CAACTCGAGA GCATGAAGGC GGAATCGCTA GTAATCGCGG ATCAGCATGC CGCGGTGAAT     1320
ACGTTCCCAG GCTTTGTACA CACCGCNCGT CACACCATGG GAGTTGGATT CACCCGAAGG     1380
CGTTGCGCCA ACCTAGCAAT AGGAAGCAGG CGACCACGGT GGGTTCAGCG ACTGGGG       1437
```

(2) INFORMATION FOR SEQ ID NO:6:

(i) SEQUENCE CHARACTERISTICS:
        (A) LENGTH: 1446 base pairs
        (B) TYPE: nucleic acid
        (C) STRANDEDNESS: double
        (D) TOPOLOGY: linear (xi) SEQUENCE DESCRIPTION: SEQ ID NO:6:

```
AGAGTTTGAT CATGGCTCAG AATGAACGCT GGCGGCATGC CTAACACATG CAAGTCGAAC      60
GAAGGCTTCG GCCTTAGTGG CGCACGGGTG GCTAACGCGT GGGAATCTGC CCTCAGGTTC     120
GGAATAACAG CGAGAAATTG CTGCTAATAC CGGATGATAT CGCGAGATCA AGATTTATC      180
GCCTGAGGAT GAGCCCGCGT AGGATTAGCT AGTTGGTGTG GTAAAGGCGC ACCAAGGCGA     240
CGATCCTTAG CTGGTCTGAG AGGATGATCA GCCACACTGG GACTGAGACA CGGCCCAGAC     300
TCCTACGGGA GGCAGCAGTG GGAATATTG  ACAATGGGC  GAAAGCCTGA TCCAGCAATG     360
CCGCGTGAGT GATGAAGGCC TTAGGGTTGT AAAGCTCTTT TACCCGGGAT GATAATGACA     420
GTACCGGGAG AATAAGCTCC GGCTAACTCC GTGCCAGCAG CCGCGGTAAT ACGGAGGGAG     480
CTAGCGTTAT TCGGAATTAC TGGGCGTAAA GCGCACGTAG GCGGCTTTGT AAGTTAGAGG     540
TGAAAGCCTG GAGCTCAACT CCAGAATTGC CTTTAAGACT GCATCGCTTG AATCCAGGAG     600
AGGTGAGTGG AATTCCGAGT GTAGAGGTGA AATTCGTAGA TATTCGGAAG AACACCAGTG     660
GCGAAGGCGG CTCACTGGAC TGGTATTGAC GCTGAGGTGC GAAAGCGTGG GGAGCAAACA     720
GGATTAGATA CCCTGGTAGT CCACGCCGTA AACGATGATA ACTAGCTGTC GGGGCTCTTA     780
GAGCTTCGGT GGCGCACGTA ACGCATTAAG TTATCCGCCT GGGGAGTACG GCCGCAAGGT     840
TAAAACTCAA ATGAATTGAC GGGGGCCTGC ACAAGCGGTG GAGCATGTGG TTTAATTCGA     900
AGCAACGCGC AGAACCTTAC CAGCGTTTGA CATGTCCGGA CGATTTCGGG AGACCGATCT     960
CTTCCCTTCG GGACTGGAA  CACAGGTGCT GCATGGCTGT CGTCAGCTCG TGTCGTGAGA    1020
TGTTGGGTTA AGTCCCGCAA CGAGCGCAAC CCTCGTCCTT AGTTGCCATC ATTTAGTTGG    1080
GCACTCTAAG GAAACCGCCG GTGATAAGCC GGAGGAAGGT GGGGATGACG TCAAGTCCTC    1140
ATGGCCCTTA CGCGCTGGGC TACACACGTG CTACAATGGC GGTGACAGTG GGCAGCAATC    1200
TCGCAAGGGT GAGCTAATCT CCAAAAGCCG TCTCAGTTCG GATTGTTCTC TGCAACTCGA    1260
GAGCATGAAG GCGGAATCGC TAGTAATCGC GGATCAGCAT GCCGCGGTGA ATACGTTCCC    1320
AGGCCTTGTA CACACCGCCC GTCACCAT   GGGAGTTGGA TTCACCCGAA GGCAGTGCGC    1380
TAACCGCAAG GAGGCAGCTG ACCACGGTGG GTTCAGCGAC TGGGGTGAAG TCGTAACAAG    1440
GTAACC                                                              1446
```